(12) United States Patent
Dehghani et al.

(10) Patent No.: US 9,546,235 B2
(45) Date of Patent: Jan. 17, 2017

(54) PEPTIDE-HYDROGEL COMPOSITE

(71) Applicant: The University of Sydney, Sydney, New South Wales (AU)

(72) Inventors: Fariba Dehghani, Sydney (AU); Anthony Steven Weiss, Sydney (AU); Hua Wei, Sydney (AU); Suzanne Marie Mithieux, Sydney (AU); Ali Fathi, Sydney (AU)

(73) Assignee: THE UNIVERSITY OF SYDNEY (AU)

(*) Notice: Subject to any disclaimer, the term of this patent is extended or adjusted under 35 U.S.C. 154(b) by 42 days.

(21) Appl. No.: 14/366,663

(22) PCT Filed: Dec. 19, 2012

(86) PCT No.: PCT/AU2012/001566
§ 371 (c)(1),
(2) Date: Jun. 18, 2014

(87) PCT Pub. No.: WO2013/091001
PCT Pub. Date: Jun. 27, 2013

(65) Prior Publication Data
US 2014/0357823 A1  Dec. 4, 2014

(30) Foreign Application Priority Data
Dec. 19, 2011  (AU) ................................ 2011905293

(51) Int. Cl.
*C08F 220/54* (2006.01)
*A61K 47/48* (2006.01)
*C08F 220/28* (2006.01)
*C08F 220/36* (2006.01)

(52) U.S. Cl.
CPC ....... *C08F 220/54* (2013.01); *A61K 47/48223* (2013.01); *A61K 47/48784* (2013.01); *C08F 220/28* (2013.01); *C08F 220/36* (2013.01); *C08F 2220/283* (2013.01); *C08F 2800/10* (2013.01)

(58) Field of Classification Search
CPC .................. A61K 47/48223; A61K 47/48784; C08F 220/28; C08F 220/36; C08F 220/54; C08F 2220/283; C08F 2800/10
USPC ................................................ 526/303.1, 262
See application file for complete search history.

(56) References Cited

U.S. PATENT DOCUMENTS

| | | | |
|---|---|---|---|
| 2006/0115457 A1 | 6/2006 | Hnojewyj | |
| 2008/0096975 A1* | 4/2008 | Guan | A61K 9/0019 514/772.3 |
| 2009/0226519 A1 | 9/2009 | Claude et al. | |
| 2010/0159008 A1 | 6/2010 | Barron et al. | |
| 2011/0223230 A1 | 9/2011 | Hersel et al. | |
| 2011/0275154 A1* | 11/2011 | Martin | C12N 5/0068 435/402 |
| 2012/0156176 A1* | 6/2012 | Fujimoto | A61K 9/0024 424/93.7 |
| 2012/0220691 A1 | 8/2012 | Shreiber et al. | |

FOREIGN PATENT DOCUMENTS

| | | | |
|---|---|---|---|
| WO | WO 01/36000 | 5/2001 | |
| WO | 01/70288 A2 | 9/2001 | |
| WO | 2008/045904 A2 | 4/2008 | |
| WO | WO 2010127254 A2 * | 11/2010 | ........... A61K 9/0024 |

OTHER PUBLICATIONS

Eastoe, J.E. "The Amino Acide Composition of Mammalian Collagen and Gelatin", Biochemical Journal, 1955, 61, 589-600. Tables 2-3, 5.
International Search Report and Written Opinion Issued in Appl. No. PCT/AU2012/001566 on Feb. 22, 2013.
Jin R. et al. "Synthesis and Characterisation of Hyaluronic acid-poly(ethylene glycol) hydrogels via Michael addition: An Injectable Biomaterial for Cartilage Repair", Acta Biomaterialia 2010, 6, 1968-1977. Abstract, sections 2, 3.1-3.2.
Moon et al. "Preparation of Biodegradable Thermo-Responsive Polyaspartamides with N-isopropylamine Pendant Groups (I)", Bulletin of the Korean Chemical Society, 2006, 27, 1981-1984.
Ward et al. "Thermoresponsive Polymers for Biomedical Applications," Polymers, Aug. 2011, 3, 1215-1242, Section 3.1.
Angel E. Mercado et al., "Release characteristics and osteogenic activity of recombinant human bone morphogenetic protein-2 grafted to novel self-assembled poly(lactide-co-glycolide fumarate) nanoparticles," Journal of Controlled Release, 140, 2009, pp. 148-156.
Cindy Chung et al., "Engineering cartilage tissue," Advanced Drug Delivery Reviews, 60, 2008, pp. 243-262.
Claire Vinatier et al., "Cartilage engineering: a crucial combination of cells, biomaterials and biofactors," Trends in Biology, vol. 27, No. 5, Mar. 2009, pp. 307-314.

(Continued)

*Primary Examiner* — Ling Choi
*Assistant Examiner* — Chun-Cheng Wang
(74) *Attorney, Agent, or Firm* — Stoel Rives LLP

(57) ABSTRACT

The present invention relates to polymers, especially polymers useful as hydrogels, and to use of hydrogels for repair or restoration of tissue. In particular, the polymers and hydrogels of the present invention can be used for the repair or restoration of cartilage, especially articular cartilage. The polymers comprise at least a monomer for binding water, a monomer for imparting mechanical properties and a monomer for binding to an extracellular protein. The hydrogels comprise a polymer comprising at least a monomer for binding water and a monomer for binding to an extracellular protein. Crosslinking polymers by binding of said extracellular matrix protein forms hydrogels.

13 Claims, 13 Drawing Sheets

(56) References Cited

OTHER PUBLICATIONS

Corrinus C. van Donkelaar et al., "Review on Patents for Mechanical Stimulation of Articular Carnage Tissue Engineering," Recent Patents on Biomedical Engineering, 2008, vol. 1, No. 1, pp. 1-12.

Dirk Schmaljohann et al., "Thermo-Responsive PNiPAAm-g-PEG Films for Controlled Cell Detachment," Biomacromolecules, vol. 4, No. 6, Nov. 1, 2003, pp. 1733-1739, XP055211143, ISSN: 1525-7797, DOI: 10.1021/bm034160p.

Extended European Search Report mailed Sep. 10, 2015 in European Patent Application No. 12859961.0.

H. Janice Lee et al., "Collagen mimetic peptide-conjugated photopolymerizable PEG hydrogel," Biomaterials, 27, 2006, pp. 5268-5276.

Jianjun Guan et al., "Protein-Reactive, Thermoresponsive Copolymers with High Flexibility and Biodegradability," Biomacromolecules, vol. 9, No. 4, 2008, pp. 1283-1292.

Marion M. Bradford, "A Rapid and Sensitive method for the Quantitation of Microgram Quantities of Protein Utilizing the Principle of Protein-Dye Binding," Analytical Biochemistry, 72, 1976, pp. 248-254.

W. N. E. van Dijk-Wolthuis et al., "A new class of polymerizable dextrans with hydrolysable groups: hydroxyethyl methacrylated dextran with and without oligolactate spacer," Polymer, vol. 38, No. 25, 1997, pp. 6235-6242.

\* cited by examiner

PEPTIDE-HYDROGEL COMPOSITE

This application is a national stage entry under 35 U.S.C §371 of international patent application no. PCT/AU2012/001566, filed on Dec. 19, 2012 which claims priority to Australian provisional patent application no. 2011905293, filed on Dec. 19, 2011, now expired, the disclosures of which are incorporated herein by reference.

FIELD OF THE INVENTION

The invention relates to polymers, especially polymers useful as hydrogels, and to the use of hydrogels for repair or restoration of tissue, in particular, for repair or restoration of cartilage, especially articular cartilage.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

Articular cartilage is a highly specialized tissue that reduces joint friction at the extremities of long bones. It is predominantly avascular, aneural and alymphatic and it consists essentially of chondrocytes, some progenitor cells and an extracellular matrix (ECM). The ECM is composed of a network of collagens, in particular type II collagen, which gives the tissue its shape and strength, and proteoglycans, which give resistance to mechanical stress. Elastin fibres are also found, predominatly in the superficial zone.

The repair of damage to articular cartilage is one of the most challenging issues of musculoskeletal medicine due to the poor intrinsic ability of cartilage for repair.[1] Natural cartilage repair is limited because chondrocyte density and metabolism are low and cartilage has no blood supply.[2]

Common treatments for cartilage repair include autologous chondrocyte transplantation (ACT), microfracture, mosaicplasty, and osteochondral allograft transplantation. ACT has been used for almost three decades to treat full-thickness chondral defects worldwide. However, inherent limitations of ACT include the low efficacy of cells due primarily to poor numbers obtained through biopsy and structural dissimilarity between the repaired tissue and native cartilage. Other drawbacks of these treatments include donor site morbidity, complicated surgical procedures, risks of infection, and graft rejection.[3]

Due to its limited ability for self repair, cartilage is an ideal candidate for tissue engineering. Since collagen itself is a natural three-dimensional scaffold for cells in vivo, collagen isolated from animals has been used for a number of tissue engineering scaffolds in vitro, both in gel or solid forms. For example, type I collagen gel, when used as a three-dimensional scaffold for cell encapsulation, enhances the stability and differentiation of encapsulated cells.

One problem with collagen is that it alone cannot provide the compressive resilience required in articular cartilage that is normally provided by proteoglycan, especially aggrecan and other water binding connective tissue molecules. Further, when crosslinked, collagen may be difficult to inject at room temperature.

Unfortunately, because of several confounding characteristics of collagen, little progress has been made in producing hybrid scaffolds that incorporate both collagen and water binding synthetic molecules. In particular, due to its loose network structure, collagen is ineffective at retaining passively adsorbed molecules, which reside mostly in the highly hydrated spaces between collagen fibers, which lack attractive forces. Other problems, such as poor mechanical strength and the lack of tissue-specific adhesion and signalling molecules, also limit the use of purified collagen as a tissue engineering scaffold. In addition, the heterogeneous chemical composition of collagen and its complex molecular architecture present significant challenges when performing chemical reactions on collagen to modulate its biochemical properties.

On the other hand, synthetic scaffolds, such as hydrogels, offer better control of the matrix architecture and chemical composition. However, a number of limitations apply to the use of hydrogels that consist of synthetic molecules. First, without collagen or other ECM components, the necessary shape and strength characteristics of articular cartilage that arise from collagen cannot be derived from a synthetic hydrogel. Second, hydrogels are formed from polymers that must initially be crosslinked before the hydrogel can form. Crosslinking is an additional manufacture step that increases likelihood of contamination of the hydrogel, particularly with toxic components, or otherwise decreases the likelihood of biocompatibility with tissue. Third, synthetic hydrogels have low biological activities and therefore are limited in the extent to which they can provide a substrate for interaction with biological elements.

To date it has been difficult to provide a scaffold in which collagen and synthetic polymer are associated with each other, so as to provide a hydrogel having the strength, shape, and compressive resilience of articular cartilage. Simply applying a composition of collagen and synthetic polymer does not work because the collagen and polymer tend to dissociate in vivo so that a useful hydrogel for repair of articular cartilage is not formed.

Lee et al.[4] describes a composite in which UV-crosslinked polymer is chemically linked to collagen modified protein (CMP). The composite forms a substrate on which cells may grow and lay down collagen. The collagen then binds to the CMP through non-covalent interactions, thereby forming a biosynthetic hydrogel composite in vivo. The problem with this approach is that it relies on cells existing in cartilage tissue to provide collagen. This either requires endogenous cells to infiltrate through articular cartilage, which is unlikely given that cartilage is essentially acellular, or the transplantation of chondrocytes or related cells. Further, the approach requires prior crosslinking of polymers to form the hydrogel.

There is a need for improved hydrogels that effectively model the shape, strength and resilience characteristics of articular cartilage.

There is a need for ECM-containing composites that effectively model the water binding and compressive resilience characteristics of articular cartilage as otherwise provided by the proteoglycan component of articular cartilage.

There is a need for synthetic hydrogels that effectively model the shape and strength characteristics of articular cartilage as otherwise provided by the collagen and ECM component of articular cartilage.

There is a need for synthetic hydrogels that can be formed without the use of chemical crosslinking, or crosslinking by UV irradiation or the like.

There is a need for hydrogels that bind to growth factors, drugs and the like, and that are a useful substrate for growth of cells thereon.

There is a need for compositions for repair of articular cartilage that are injectable at room temperature and that form a hydrogel at body temperature.

SUMMARY OF THE INVENTION

The invention seeks to address, or at least to provide an improvement to, one or more of the above mentioned limitations, needs or problems and in one embodiment provides a polymer for forming a hydrogel. The polymer includes:
a first monomer for binding water;
a second monomer for imparting mechanical properties to a hydrogel; and
a third monomer for binding to an extra-cellular matrix protein.

In certain embodiments, the polymer further includes:
a fourth monomer for imparting phase transition characteristics to a hydrogel enabling injection at room temperature, and gel formation at body temperature.

In other embodiments there is provided a composition for forming a hydrogel. The composition includes:
an extra-cellular matrix protein; and
a polymer;
wherein the polymer includes:
a first monomer for binding water; and
a second monomer that is bound to the extra-cellular matrix protein;
wherein the binding of the extra-cellular matrix protein to the second monomer crosslinks the polymer, thereby enabling formation of a hydrogel when the composition is contacted with water.

In certain embodiments, the polymer further includes:
a third monomer for imparting mechanical properties to a hydrogel.

This third monomer enables the polymer to contribute additional mechanical properties (such as strength and resilience) to the hydrogel.

In additional embodiments, the polymer further includes:
a fourth monomer for imparting phase transition characteristics to a hydrogel enabling injection at room temperature, and gel formation at body temperature.

In yet further embodiments there is provided a hydrogel including:
water;
an extra-cellular matrix protein; and
a polymer;
wherein the polymer includes:
a first monomer for binding water; and
a second monomer that is bound to the extra-cellular matrix protein;
wherein the binding of the extra-cellular matrix protein to the second monomer crosslinks the polymer, thereby forming the hydrogel.

In certain embodiments, the polymer further includes:
a third monomer for imparting mechanical properties to a hydrogel.

As mentioned above, this enables the polymer to contribute additional mechanical properties (such as strength and resilience) to the hydrogel.

In additional embodiments, the polymer further includes:
a fourth monomer for imparting phase transition characteristics to a hydrogel enabling injection at room temperature, and gel formation at body temperature.

In other embodiments there are provided methods and uses of the polymer and composition described above for forming a hydrogel, and uses of the hydrogel for repairing or restoring articular cartilage.

DETAILED DESCRIPTION OF THE EMBODIMENTS

Figure 1:
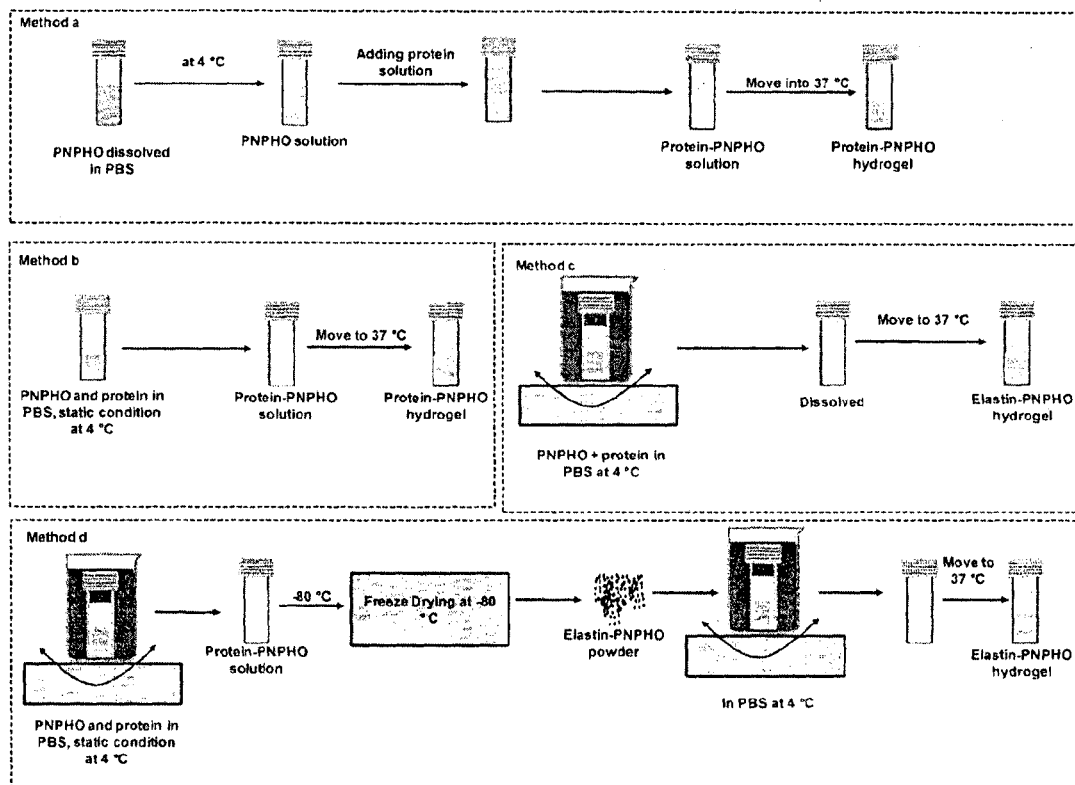
FIG. 1. Different methods for conjugation of protein and PNPHO for formation of protein-PNPHO hydrogels.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps.

Recognising the above limitations in the field of biocompatible synthetic hydrogels, the inventors have designed a new polymer that enables formation of a hydrogel useful for repair of articular cartilage. Key considerations in the design of the polymer have been to ensure that (i) all components of the hydrogel can be delivered from external sources and without reliance on cell or tissue machinery; (ii) the components, in particular synthetic polymer and extra-cellular matrix protein (ECMP) are bound so that they do not dissociate in vivo; (iii) chemical and UV crosslinking is not required; (iv) the hydrogel is injectable at room temperature; (v) the hydrogel is a compatible substrate for cells and tissue.

In designing the polymer, the inventors have recognised that an as yet unexploited potential of protein-based polymers such as collagen as a crosslinker of synthetic polymers could be realised by incorporating a monomer having a functional group for binding to collagen or other ECMPs into a synthetic polymer, thereby enabling the ECMP to crosslink the polymer for formation of hydrogel scaffolds that can be used for tissue engineering, and in particular in cartilage repair and regeneration. The hydrogels of the present invention are formed by simply combining an ECMP (e.g. collagen) with a hydrophilic polymer that is capable of binding to the ECMP. Therefore, the hydrogels of the present invention can be formed without the use of any additional agents (e.g. crosslinking initiators) or special conditions (e.g. irradiation of the polymers with UV and/or IR radiation) to effect the crosslinking of the polymers, while still providing a scaffold that can be used to encapsulate cells and other ECM components to assist in cartilage repair and regeneration, upon administration of the hydrogel to the desired site. The hydrogel of the present invention also has the added advantage of being easily administrable (e.g. via injection) directly to the desired site, due to its phase-transition properties.

The advantageous properties of the hydrogels of the present invention can be attributed to the combination of ECMPs and the particular components of the polymers of the present invention. In particular, the polymers of the present invention possess the required water-binding capacity and crosslinking ability (which can also be referred to as conjugation ability), such that they are able to bind to ECMPs and form hydrogels containing the ECMPs, in addition to having, in some embodiments, particular components that contribute to the strength, shape, resilience and phase-transfer properties of the hydrogel, once formed. The ECMPs, in addition to providing an environment that mimics, to some extent, the natural environment of the tissue to be replaced and/or repaired, also provide the requisite strength and shape to the hydrogels of the present invention. This is particularly important in applications such as cartilage repair and replacement, where hydrogels need to withstand the stresses commonly placed on cartilage-bearing regions, such as joints.

The present inventors have developed polymers having the desired characteristics for use in hydrogels intended for tissue repair, and in particular those hydrogels intended for repair and/or replacement of cartilage, by combining components that either inherently possess some of these characteristics, or that can provide such characteristics to the hydrogel once it is formed. Accordingly, the polymers of the present invention include, within their structure, particular units (e.g. monomers, macromonomers, and the like) that have been chosen based on their ability to convey the desired water-binding, crosslinking, strength, resilience and phase-transfer properties to the polymers of the present invention, and subsequently to the hydrogels formed from such polymers. In addition, the properties of these polymers (and therefore the hydrogels formed from these polymers) can be tuned, in the sense that different monomers, as well as different proportions of these monomers, can be selectively incorporated into the polymers These advantageous properties of the hydrogels of the present invention are discussed throughout the present specification, and in particular, are exhibited in the Examples, which show that hydrogels of the present invention can be made in a simple manner using a simple combination of the polymers of the present invention with ECMPs, and that the hydrogels thus formed possess the required properties of strength, resilience and shape, that enables them to be used in tissue engineering applications.

A. Polymers

The term "polymer", as used herein, refers to a large molecule (macromolecule) composed of repeating structural units (monomers). These subunits are typically connected by covalent chemical bonds. Polymers can be linear or branched polymers. Preferably, the polymers of the present invention are copolymers comprising three or more different monomers.

Accordingly, in one embodiment, the polymer of the present invention includes a first water-binding monomer, a second monomer that is capable of imparting mechanical properties to a hydrogel, and a third monomer that has a functional group for binding to an ECMP.

The term "monomer", as used herein, refers to a structural unit that can be combined to form a polymer, but that itself may also be a polymer, or a derivative of a monomer or polymer. Monomers of this type are herein also referred to as "macromonomers".

A1. Water-Binding Monomers

As discussed above, the advantageous properties of the hydrogels of the present invention can be attributed to the combination of ECMPs and the particular components of the polymers of the present invention. One particular advantageous property of the polymers of the present invention is their water-binding capacity. The presence of water in the hydrogels of the present invention provides both an environment that resembles the natural environment of the damaged tissue (which assists in tissue regeneration), and the required compression resistance to the hydrogel.

Accordingly, the polymers of the present invention should include monomers or units that are able to bind water to such a capacity that a hydrogel is able to form when the polymer is contacted with an ECMP and water. In addition, the hydrogel thus formed should have the required compression resistance and resilience. This is important for applications such as cartilage repair and restoration, because, as discussed above, cartilage is commonly subjected to significant mechanical stresses.

A person skilled in the art will understand that water-binding monomers need to be present in the polymers of the present invention in proportions that are sufficient to produce a polymer that fulfils these requirements. Generally, the proportion of water-binding monomers in the polymer is about 10:1, about 5:1, about 4:1, about 3:1, about 2:1, about 1:1, about 1:2, about 1:3, about 1:4, about 1:5 molar ratio of water binding:mechanical strength monomers. In fact, the water-binding monomers need to make the polymer not only hydrophilic, but impart much more significant water-binding capacities to the polymer. Accordingly, polymers in accordance with the present invention will have water-binding capacities of between about 70% and about 500%, between about 80% and about 400%, between about 90% and about 300% or between about 100% and about 200%. For example, the water-binding capacity of the polymers of the present invention is about 70%, about 80%, about 90%, about 100%, about 110%, about 120%, about 130%, about 140%, about 150%, about 160%, about 170%, about 180%, about 190%, about 200%, about 210%, about 220%, about 230%, about 240%, about 250%, about 260%, about 270%, about 280%, about 290%, about 300%, about 310%, about 320%, about 330%, about 340%, about 350%, about 360%, about 370%, about 380%, about 390%, about 400%, about 410%, about 420%, about 430%, about 440%, about 450%, about 460%, about 470%, about 480%, about 490%, or about 500%.

Suitable examples of water-binding monomers include those that can be synthesised into polymers such as polyethers (e.g., alkylene polyoxides such as polyethylene glycol (PEG), oligo(ethylene glycol) (OEG), polyethylene oxide (PEO), polyethylene oxide-co-propylene oxide (PPO), co-polyethylene oxide block or random copolymers, polyvinyl alcohol (PVA)), poly(vinyl pyrrolidinone) (PVP), poly(amino acids) and dextran. The polyethers, and more particularly oligo(oxyalkylenes) (e.g. OEG), are especially preferred, because they have the requisite water-binding capacity, are simple to synthesise and/or purchase, and are inert, in the sense that they illicit minimal or no immune response from the tissues into which they are placed. In addition, any of a variety of hydrophilic functionalities can be used to make a monomer (and therefore a polymer formed from such a monomer) water soluble. For example, functional groups like phosphate, sulphate, quaternary amine, hydroxyl, amine, sulfonate and carboxylate, which are water soluble, may be incorporated into a monomer to make it water soluble.

A2. Imparting Mechanical Properties

As discussed above, the advantageous properties of the hydrogels of the present invention can be attributed, in part, to the particular components that make up the polymers of the present invention. In some embodiments, the polymers of the present invention are able to contribute additional mechanical properties to the hydrogels of the present invention, which produces hydrogels that, due to their strength and resilience, can be used in the repair and restoration of tissues (e.g. cartilage) that reside in high-stress environments, such as joints.

Accordingly, the polymers of the present invention may include monomers or units that are able to provide strength and resilience required in articular cartilage. This is important for applications such as cartilage repair and restoration, because, as discussed above, cartilage is commonly subjected to significant mechanical stresses.

A person skilled in the art will understand that monomers capable of imparting mechanical properties to a hydrogel need to be present in the polymers of the present invention in proportions that are sufficient to produce a hydrogel having the desired mechanical properties. Generally, the proportion of "mechanical" monomers in the polymer is about 10:1, about 5:1, about 4:1, about 3:1, about 2:1, about 1:1, about 1:2, about 1:3, about 1:4, about 1:5 molar ratio of water binding:mechanical strength monomers.

Suitable examples of monomers that are capable of imparting mechanical properties (e.g. compression resistance) to a hydrogel include acrylates such as hydroxyethyl methacrylate (HEMA), polyesters such as poly(lactic acid), poly(caprolactone), poly(glycolide), and their random co-polymers (e.g. poly(glycolide-co-lactide) and poly(glycolide-co-caprolactone)).

A3. ECMP Binding

As discussed above, the hydrogels of the present invention form by combining a polymer of the present invention with an ECMP, in the presence of water. In order to effectively combine the polymers of the present invention with an ECMP, the inventors have included, in the polymers of the present invention, monomers or units that have a crosslinking ability.

This crosslinking ability means that the polymers are able to bind to ECMPs (as discussed further below) and, by doing so, crosslink the ECMPs to form hydrogels containing the ECMPs. Alternatively, via a similar mechanism, the ECMPs act as the crosslinker, thereby crosslinking the polymer to form a hydrogel.

By devising a unique polymer design whereby a monomer having a functional group for binding with collagen, elastin or the like is provided in the polymer, the inventors have recognised that polymers do not need to be further crosslinked with, for example, chemical or UV crosslinking, to form a hydrogel.

In addition, by covalently binding the ECMP to the polymer, the ECMP is more effectively retained in the hydrogel network, which means that, once the hydrogel is administered to the repair site, the ECMP is not able to migrate easily away from the site. This means that the structural integrity of the gel at the repair site is maintained (due to the mechanical properties of ECMPs, as mentioned above), and assists in providing an environment at the repair site that closely mimics the natural environment of the tissue.

In order to produce a polymer that is capable of binding to an ECMP, a person skilled in the art will understand that monomers capable of binding to an ECMP need to be present in the polymers of the present invention in proportions that are sufficient to crosslink with an ECMP, such that a hydrogel can be formed in the presence of water. Generally, the proportion of "crosslinking" monomers in the polymer is at least about 1:1 molar ratio of crosslinking monomer:water binding monomer. This ratio can increase to, for example, about 2:1, about 3:1, about 4:1, about 5:1, about 6:1, about 7:1, about 8:1, about 9:1 and about 10:1.

Monomers that are capable of binding to ECMPs generally have either electrophilic or nucleophilic functional groups, such that a nucleophilic functional group on, for example, an ECMP may react with an electrophilic functional group on the monomer, to form a covalent bond. Preferably, the polymer comprises more than two ECMP-binding monomers, so that, as a result of electrophilic-nucleophilic reactions, the polymer combines with the ECMP to form crosslinked polymeric products. Such reactions are referred to as "crosslinking reactions".

Therefore, for example, if an ECMP has nucleophilic functional groups such as amines, the polymer may have electrophilic functional groups such as N-hydroxysuccinimides (NHS). Other electrophilic functional groups that are suitable for use in the present invention are N-hydroxysulfosuccinimide (SNHS) and N-hydroxyethoxylated succinimide (ENHS). An example of a monomer of this type is N-acryloxysuccinimide (NAS). On the other hand, if an ECMP has electrophilic functional groups, then the polymer may have nucleophilic functional groups such as amines or thiols.

A4. Phase-Transition Monomers

In another embodiment of the present invention, the polymer may further include a fourth monomer that is capable of imparting phase transition characteristics to the hydrogel, thereby enabling the composite to be in an injectable form at room temperature, and in a hydrogel form at body temperature. Further, these phase-transition characteristics allow the polymers of the present invention to form hydrogels, of which various properties (such as viscosity) can be varied by altering factors such as pH and temperature. Thermo-responsive injectable hydrogels are designed such that the lower critical solution temperature (LOST) is below body temperature. Therefore, gelation can be achieved simply by increasing the temperature of the hydrogel by, for example, letting it warm up to body temperature (which occurs when the hydrogel is administered into the body). Various thermo-responsive and injectable polymers including poly(ethylene oxide)/poly(propylene oxide) and poly(N-isopropylacrylamide) (PNIPAAm) copolymers are suitable for use in the present invention. PNIPAAm is particularly suitable, as it has a LCST of 32° C., allowing it to be in the gel form at body temperature.

In order to produce a polymer that is thermoresponsive, a person skilled in the art will understand that the phase-transition monomers need to be present in the polymers of the present invention in proportions that are sufficient to enable the viscosity of a hydrogel including the polymer to be varied by exposure of the hydrogel to different conditions of temperature and pH. Generally, the proportion of "phase-transition" monomers in the polymer is at least about 9:1 molar ratio of phase-transition monomer:water binding monomer. This ratio can increase to, for example, about 10:1, about 11:1, about 12:1, about 13:1, about 14:1, about 15:1, about 16:1, about 17:1, about 18:1, about 19:1, about 20:1, about 21:1, about 22:1, about 23:1, about 24:1, about 25:1, about 26:1, about 27:1, about 28:1, about 29:1 and about 30:1 molar ratio of phase-transition monomer:water binding monomer.

The present inventors have found that the viscosity of the hydrogels of the present invention, at lower temperatures (e.g. 4° C.), is such that the hydrogel is injectable. The hydrogel then becomes more viscous as the temperature increases, forming a gel having the desired viscosity at a temperature of about 37° C. This means that the hydrogel of the present invention, at cooler temperatures, can be administered easily to the site of repair by, for example, injection. The hydrogel is then transformed, by warming in the body to the body's natural temperature, into a more viscous gel, which has the desired strength and elasticity properties.

A5. Other Polymer Properties and Synthesis of Polymers

It will be understood by a person skilled in the art that, by combining different types of monomers, polymers can be produced that have a range of different properties. In addition, by incorporating particular monomers or functional groups into a pre-existing polymer, the properties of the polymer can be modified. For example, co-polymerization of HEMA monomers with other monomers (such as methyl methacrylate) can be used to modify properties such as swelling and mechanical properties. Monomers may also be reacted with other compounds to form "macromonomers" (mentioned above) that are then included in the polymers of the present invention. For example, HEMA can be reacted with lactide to form a HEMA-poly-lactic acid polymer (HEMA-PLA), which itself can be used as a monomer in the polymers of the present invention. In addition, the monomers themselves may be combinations of monomer units, which are then incorporated into the polymer. An example of this type of monomer is oligo(ethylene glycol) monomethyl ether methacrylate (OEGMA), which is a hydrophilic monomer composed of two hydrophilic monomers: ethylene glycol and methacrylate.

The polymers of the present invention may be further modified with one or more moieties and/or functional groups. Any moiety or functional group can be used in accordance with the present invention. In some embodiments, polymers may be modified with polyethylene glycol (PEG), with a carbohydrate, and/or with acyclic polyacetals derived from polysaccharides. In addition, as discussed above, hydrophilic groups can be incorporated into monomers (and therefore polymers) to increase a polymer's water-binding capacity.

In terms of sequence, copolymers may be block copolymers, graft copolymers, random copolymers, blends, mixtures, and/or adducts of any of the foregoing and other polymers. Typically, polymers in accordance with the present invention are organic polymers. Preferably, the polymers of the present invention are biocompatible. In some embodiments, the polymers are biodegradable. In other embodiments, the polymers are both biocompatible and biodegradable.

The polymers of the present invention may also include other monomers in their structure. For example, the monomers may be polymers such as poly(vinyl alcohol) (PVA), polyesters, acrylic polymers and ionic polymers, or monomers of these.

If it is desired that the polymer be biodegradable or absorbable, one or more monomers having biodegradable linkages may be used. In the alternative, or in addition, the monomers may be chosen such that the product of the reaction between them results in a biodegradable linkage. For each approach, monomers and/or linkages may be chosen such that the resulting biodegradable polymer will degrade or be absorbed in a desired period of time. Preferably, the monomers and/or linkages are selected such that, when the polymer degrades under physiological conditions, the resulting products are non-toxic.

The biodegradable linkage may be chemically or enzymatically hydrolyzable or absorbable. Illustrative chemically-hydrolysable biodegradable linkages include polymers, copolymers and oligomers of glycolide, lactide, caprolactone, dioxanone, and trimethylene carbonate. Illustrative enzymatically-hydrolysable biodegradable linkages include peptidic linkages cleavable by metalloproteinases and collagenases. Additional illustrative biodegradable linkages include polymers and copolymers of poly(hydroxy acid)s, poly(orthocarbonate)s, poly(anhydride)s, poly(lactone)s, poly(aminoacid)s, poly(carbonate)s, and poly(phosphonate)s.

In one embodiment, the polymer of the present invention is a polymer of formula (I):

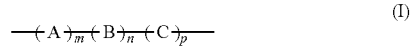

(I)

wherein A is a water-binding monomer, B is a monomer that is capable of imparting mechanical properties to a hydrogel, C is a monomer that has a functional group for binding to an ECMP, m is an integer from 1 to 10, n is an integer from 1 to 10, and p is an integer from 1 to 10.

The polymer of the present invention may accordingly be a polymer of formula (Ia):

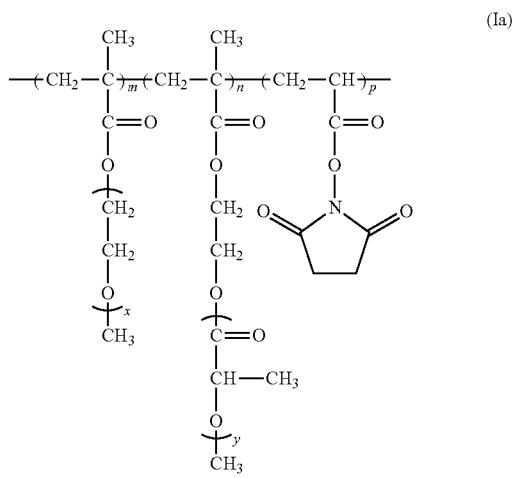

wherein A is the water-binding monomer OEGMA, B is the strengthening monomer HEMA-PLA, C is the crosslinker NAS, m, n and p are as defined above, x is an integer from 1 to 1000, and y is an integer from 1 to 1000.

When the polymer of the present invention includes a fourth monomer that is capable of imparting phase transition characteristics to the hydrogel, the polymer may be a polymer of the formula (II):

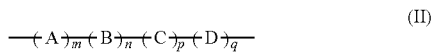

wherein A, B, C, m, n, and p are as defined above, D is a monomer that is capable of imparting phase transition characteristics to the hydrogel, and q is an integer from 1 to 10. An example of such a polymer is a polymer of formula (IIa):

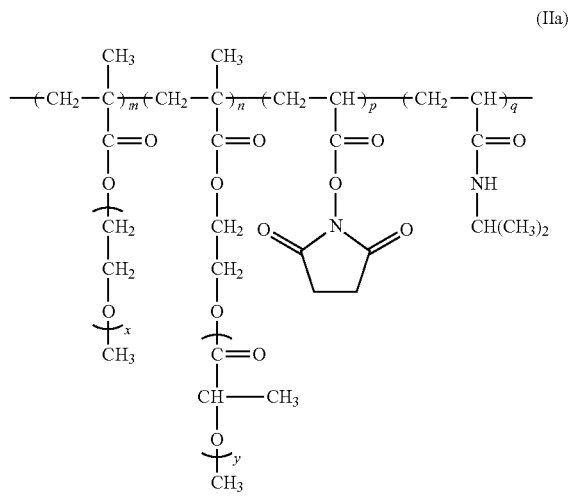

wherein A is the water-binding monomer OEGMA, B is the strengthening monomer HEMA-PLA, C is the crosslinker NAS, D is the phase-transition monomer NIPAAm, and m, n, p, q, x and y are as defined above.

The present inventors have also found that some monomers, such as HEMA-PLA, polyesters such as poly(lactic acid), poly(caprolactone), poly(glycolide), and their random copolymers (e.g. poly(glycolide-co-lactide) and poly(glycolide-co-caprolactone) and other biodegradable and biocompatible polymers, can elevate the LCST of the polymer during degradation of biodegradable segments (e.g. PLA) in vivo, leading to bioresorption of the polymer. This provides the additional advantage that the polymers of the present invention may be designed so as to be biodegradable in vivo.

A person skilled in the art will be aware that the monomers A, B, C and D may be present in the polymer in any order, provided that the required water-binding, strengthening and/or cross-linking capabilities are achieved.

The overall size of the polymer of the present invention may differ, depending on factors, such as the types of monomers that are incorporated into the polymer, the type of ECMP that is sought to be used to form the hydrogel, and the conditions under which the protein is to be coupled to the polymer. However, in general, the polymer of the present invention may be a molecule of about 1 to about 100 kDa, about 5 to about 60 kDa, or about 30 kDa.

As used herein a wording defining the limits of a range or length such as, for example, "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range.

A person skilled in the art will be aware of suitable methods of synthesising the polymers of the present invention. These include methods such as ring-opening polymerisation, addition polymerization (including free radical polymerization) and condensation polymerization.

B. Compositions for Forming Hydrogels

The present invention also relates to a composition for forming a hydrogel, the composition including an extracellular matrix protein and a polymer, the polymer including:
 a first water-binding monomer; and
 a second monomer that has a functional group that is bound to the extra-cellular matrix protein;
wherein the binding of the extra-cellular matrix protein to the second monomer crosslinks the polymer, thereby enabling formation of a hydrogel when the composition is contacted with water.

The term "composition", as used herein, refers to a solid or liquid composition containing the components mentioned above. In some embodiments, other components such as pharmaceutically-acceptable excipients and biologically active agents (e.g. drugs, vitamins and minerals), to assist in repair and/or re-generation of the target tissue, and/or to provide a method of achieving targeted delivery of biologically active compounds, may also be included in the compositions of the present invention.

In general, the amount of polymer in the composition of the present invention is an amount that allows for the formation of hydrogels in accordance with the present invention. In some embodiments, the amount of polymer in the composition of the present invention ranges between about 1% w/w and about 90% w/w, between about 2% w/w and about 80% w/w, between about 4% w/w and about 70% w/w, between about 5% w/w and about 60% w/w, between about 5% w/w and about 50% w/w, between about 6% w/w and about 40% w/w, between about 7% w/w and about 30% w/w or between about 8% w/w and about 20% w/w. In some embodiments, the amount of polymer is about 1% w/w, about 2% w/w, about 3% w/w, about 4% w/w, about 5% w/w, about 6% w/w, about 7% w/w, about 8% w/w, about 9% w/w, about 10% w/w, about 15% w/w, about 20% w/w, about 25% w/w, about, 30% w/w, about 35% w/w, about 40% w/w, about 45% w/w, about 50% w/w, about 55% w/w, about 60% w/w, about 65% w/w, about 70% w/w, about 75% w/w, about 80% w/w or more. In some embodiments, the amount of polymer is approximately 85% w/w. As a general rule, the solidity of the hydrogel increases with higher polymer concentrations in the composition.

B1. Excipients and Biologically-Active Agents

Pharmaceutically-acceptable excipients may be included in the compositions and/or hydrogels of the present invention, and include any and all solvents, dispersion media, inert diluents, or other liquid vehicles, dispersion or suspension aids, granulating agents, surface active agents, disintegrating agents, isotonic agents, thickening or emulsifying agents, preservatives, binding agents, lubricants, buffering agents, oils, and the like, as suited to the particular dosage form desired. Remington[5] discloses various excipients used in formulating pharmaceutical compositions and known techniques for the preparation thereof. Except insofar as any conventional excipient is incompatible with a substance or its derivatives, such as by producing any undesirable biological effect or otherwise interacting in a deleterious manner with any other component(s) of the pharmaceutical composition, its use is contemplated to be within the scope of this invention.

Excipients such as colouring agents, coating agents, sweetening, flavouring, and perfuming agents can be present in the composition, according to the judgment of the formulator.

Biologically active agents or drug compounds that may be added to the composition and/or hydrogel of the present invention include proteins, glycosaminoglycans, carbohydrates, nucleic acids and inorganic and organic biologically active compounds, such as enzymes, antibiotics, anti-neoplastic agents, local anesthetics, hormones, angiogenic agents, anti-angiogenic agents, growth factors (e.g. insulin-like growth factor-1 (IGF-1), basic fibroblast growth factor (bFGF) and transforming growth factor-b (TGFb)), antibodies, neurotransmitters, psychoactive drugs, anticancer drugs, chemotherapeutic drugs, drugs affecting reproductive organs, genes, and oligonucleotides.

A composition containing components such excipients and/or biologically active agents can be produced by combining a polymer of the present invention with an ECMP, drying the resulting composition, and then combining this with one or more other components. The resulting composition may be in the form of a powder or other particulate form, to which water is then added to form a hydrogel, in accordance with the present invention. A hydrogel containing these components can therefore be produced simply by adding the desired aqueous solvent to the composition.

The amount of polymer, ECMP and biologically active agent present in the composition will necessarily depend upon the particular drug and the condition to be treated. A person skilled in the art will be aware of appropriate agents and amounts to use to treat the condition.

B2. Ecmps

As used herein, the term "extra-cellular matrix protein" (or ECMP) refers to proteins that are naturally present in the extracellular part of animal tissue that provides structural support to the animal cells (in addition to performing various other important functions). The extracellular matrix (or ECM) is the defining feature of connective tissue in animals. Proteins commonly found in the ECM include collagen, elastin, fibrin, fibronectin, and laminin (and isoforms thereof).

In the context of the present invention, ECMP is important because, as discussed above, it crosslinks polymers, which enables the polymers to form a hydrogel. The hydrogels of the present invention may be formed by, for example, exposing collagen or elastin to a polymer of formula (I). ECMP is also important because it provides additional mechanical properties (such as strength and resilience) to the hydrogel, as well as providing, at the repair site, an environment that mimics the natural environment, thereby assisting in tissue repair and re-generation.

In one embodiment the ECMP may be in the form of a monomer. An example is tropoelastin. In another embodiment, the ECMP may be in the form of crosslinked monomers. An example is elastin. In yet further embodiments, the ECMP may be a combination of a range of different isoforms, for example, collagen type 1, 2, 3, 4, or a range of different proteins, for example, collagen and elastin etc.

It is important that the ECMP contains side chains or other functional groups that are exposed to enable reaction with the functional group of the ECMP-binding monomer(s), thereby binding the ECMP to the polymer through the ECMP-binding monomer(s). Examples of suitable side chains include glutamic acid or lysyl side chains.

The present invention also includes variants of the ECMPs, for example species variants or polymorphic variants. The present invention is intended to cover all functionally active variants of the ECMPs that exhibit the same activity. This also includes apo- and holo-forms of the ECMPs, post-translationally modified forms, as well as glycosylated or de-glycosylated derivatives. Such functionally active fragments and variants include, for example, those having conservative amino acid substitutions.

In general, the amount of ECMP in the composition of the present invention is an amount that allows for the formation of hydrogels in accordance with the present invention. In some embodiments, the amount of ECMP in the composition of the present invention ranges between about 1% w/w and about 60% w/w, between about 1% w/w and about 50% w/w, between about 1% w/w and about 40% w/w, between about 5% w/w and about 30% w/w, between about 5% w/w and about 20% w/w, or between about 5% w/w and about 10% w/w. In some embodiments, the percent of ECMP is about 1% w/w, about 2% w/w, about 3% w/w, about 4% w/w, about 5% w/w, about 6% w/w, about 7% w/w, about 8% w/w, about 9% w/w, about 10% w/w, about 20% w/w, about 30% w/w, about 40% w/w, about 50% w/w, or more.

Preferably, the ECMPs for use in the present invention will be obtained from recombinant sources, although they can also be extracted from natural sources or synthesised.

C. Hydrogels

The present invention also relates to a hydrogel including water, an extra-cellular matrix protein and a polymer, the polymer including:
 a first water-binding monomer; and
 a second monomer that is bound to the extra-cellular matrix protein;
wherein the binding of the extra-cellular matrix protein to the second monomer crosslinks the polymer, thereby forming a hydrogel, with the water contained therein.

In one embodiment, the hydrogel includes a polymer having a monomer described above for enabling phase transition of the hydrogel from liquid state at lower temperature to gel state at body temperature. One example of a monomer useful for this purpose is NIPAAM. It is a particularly surprising finding that an otherwise insoluble molecule, such as elastin or collagen, can be made to transition from liquid to gel state according to temperature profile by use of this monomer. Therefore, the advantage is that hydrogel of the present invention, at cooler temperatures, can be administered easily by, for example, injection. The hydrogel is then transformed into a more viscous gel, which has the desired strength and elasticity properties, following warming in the body to the natural body temperature.

Having been provided with a polymer composition described above, the hydrogel may be formed by adding water to the composition in any way known to a person skilled in the art. Indeed, one advantage of the present invention is that the polymer does not need to be crosslinked in any way prior to contact with the ECMP, in order for a hydrogel to form.

C1. Cells

The hydrogel of the present invention may also include cells to assist in repair and/or re-generation of the target tissue.

In general, cells to be used in accordance with the present invention are any types of cells. The cells should be viable when encapsulated within the hydrogels of the present invention. In some embodiments, cells that can be encapsulated within hydrogels in accordance with the present invention include, but are not limited to, mammalian cells (e.g. human cells, primate cells, mammalian cells, rodent cells, etc.), avian cells, fish cells, insect cells, plant cells, fungal cells, bacterial cells, and hybrid cells. In some embodiments, exemplary cells that can be encapsulated within hydrogels include stem cells, totipotent cells, pluripotent cells, and/or embryonic stem cells. In some embodiments, exemplary cells that can be encapsulated within hydrogels in accordance with the present invention include, but are not limited to, primary cells and/or cell lines from any tissue. For example, cardiomyocytes, myocytes, hepatocytes, keratinocytes, melanocytes, neurons, astrocytes, embryonic stem cells, adult stem cells, hematopoietic stem cells, hematopoietic cells (e.g. monocytes, neutrophils, macrophages, etc.), ameloblasts, fibroblasts, chondrocytes, osteoblasts, osteoclasts, neurons, sperm cells, egg cells, liver cells, epithelial cells from lung, epithelial cells from gut, epithelial cells from intestine, liver, epithelial cells from skin, etc, and/or hybrids thereof, may be encapsulated within hydrogels in accordance with the present invention.

Exemplary mammalian cells that can be encapsulated within hydrogels in accordance with the present invention include, but are not limited to, Chinese hamster ovary (CHO) cells, HeLa cells, Madin-Darby canine kidney (MDCK) cells, baby hamster kidney (BHK cells), NSO cells, MCF-7 cells, MDA-MB-438 cells, U87 cells, A172 cells, HL60 cells, A549 cells, SP10 cells, DOX cells, DG44 cells, HEK 293 cells, SHSY5Y, Jurkat cells, BCP-1 cells, COS cells, Vero cells, GH3 cells, 9L cells, 3T3 cells, MC3T3 cells, C3H-10T1/2 cells, NIH-3T3 cells, and C6/36 cells.

In some embodiments, it is desirable that cells are evenly distributed throughout a hydrogel. Even distribution can help provide more uniform tissue-like hydrogels that provide a more uniform environment for encapsulated cells. In some embodiments, cells are located on the surface of a hydrogel. In some embodiments, cells are located in the interior of a hydrogel. In some embodiments, cells are layered within a hydrogel. In some embodiments, the hydrogel contains different cell types.

In some embodiments, the conditions under which cells are encapsulated within hydrogels are altered in order to maximize cell viability. In some embodiments, for example, cell viability increases with lower polymer concentrations. In some embodiments, cells located at the periphery of a hydrogel tend to have decreased viability relative to cells that are fully-encapsulated within the hydrogel. In some embodiments, conditions (e.g. pH, ionic strength, nutrient availability, temperature, oxygen availability, osmolarity, etc) of the surrounding environment may need to be regulated and/or altered to maximize cell viability.

In some embodiments, cell viability can be measured by monitoring one of many indicators of cell viability. In some embodiments, indicators of cell viability include, but are not limited to, intracellular esterase activity, plasma membrane integrity, metabolic activity, gene expression, and protein expression. To give but one example, when cells are exposed to a fluorogenic esterase substrate (e.g. calcein AM), live cells fluoresce green as a result of intracellular esterase activity that hydrolyzes the esterase substrate to a green fluorescent product. To give another example, when cells are exposed to a fluorescent nucleic acid stain (e.g. ethidium homodimer-1), dead cells fluoresce red because their plasma membranes are compromised and, therefore, permeable to the high-affinity nucleic acid stain.

In general, the amount of cells in a composition is an amount that allows for the formation of hydrogels in accordance with the present invention. In some embodiments, the amount of cells that is suitable for forming hydrogels in accordance with the present invention ranges between about 0.1% w/w and about 80% w/w, between about 1.0% w/w and about 50% w/w, between about 1.0% w/w and about 40% w/w, between about 1.0% w/w and about 30% w/w, between about 1.0% w/w and about 20% w/w, between about 1.0% w/w and about 10% w/w, between about 5.0% w/w and about 20% w/w, or between about 5.0% w/w and about 10% w/w. In some embodiments, the amount of cells in a composition that is suitable for forming hydrogels in accordance with the present invention is approximately 5% w/w. In some embodiments, the concentration of cells in a precursor solution that is suitable for forming hydrogels in accordance with the invention ranges between about 10 and about $1 \times 10^8$ cells/mL, between about 100 and about $1 \times 10^7$ cells/mL, between about $1 \times 10^3$ and about $1 \times 10^6$ cells/mL, or between about $1 \times 10^4$ and about $1 \times 10^5$ cells/mL. In some embodiments, a single hydrogel comprises a population of identical cells and/or cell types. In some embodiments, a single hydrogel comprises a population of cells and/or cell types that are not identical. In some embodiments, a single hydrogel may comprise at least two different types of cells. In some embodiments, a single hydrogel may comprise 3, 4, 5, 10, or more types of cells. To give but one example, in some embodiments, a single hydrogel may comprise only embryonic stem cells. In some embodiments, a single hydrogel may comprise both embryonic stem cells and hematopoietic stem cells.

C2. Media

Any of a variety of cell culture media, including complex media and/or serum-free culture media, that are capable of supporting growth of the one or more cell types or cell lines may be used to grow and/or maintain cells. Typically, a cell culture medium contains a buffer, salts, energy source, amino acids (e.g., natural amino acids, non-natural amino acids, etc), vitamins, and/or trace elements. Cell culture media may optionally contain a variety of other ingredients, including but not limited to, carbon sources (e.g., natural sugars, non-natural sugars, etc), cofactors, lipids, sugars, nucleosides, animal-derived components, hydrolysates, hormones, growth factors, surfactants, indicators, minerals, activators of specific enzymes, activators inhibitors of specific enzymes, enzymes, organics, and/or small molecule metabolites. Cell culture media suitable for use in accordance with the present invention are commercially available from a variety of sources, e.g., ATCC (Manassas, Va.). In certain embodiments, one or more of the following media are used to grow cells: RPMI-1640 Medium, Dulbecco's Modified Eagle's Medium, Minimum Essential Medium Eagle, F-12K Medium, Iscove's Modified Dulbecco's Medium.

Those skilled in the art will recognize that the cells listed herein represent an exemplary, not comprehensive, list of cells that can be encapsulated within a precursor solution (and, therefore, eventually in a hydrogel) in accordance with the present invention.

D. Treatment of Articular Cartilage

A therapeutically effective amount of a hydrogel of the present invention may be delivered to a patient and/or organism prior to, simultaneously with, and/or after diagnosis with a disease, disorder, and/or condition. In some embodiments, a therapeutically-effective amount of a hydrogel of the present invention is delivered to a patient and/or organism prior to, simultaneously with, and/or after onset of symptoms of a disease, disorder, and/or condition.

Accordingly, in one embodiment, the present invention relates to a method of repairing biological tissue, comprising administration of a therapeutically effective amount of a hydrogel of the present invention.

The present invention also relates to the use of a therapeutically effective amount of a composition of the present invention or a hydrogel of the present invention for repairing biological tissue.

The present invention also provides a composition of the present invention or a hydrogel of the present invention for use in the repair of biological tissue, in any of the embodiments described in the specification.

The present invention also relates to the use of a therapeutically effective amount of a hydrogel of the present invention or a composition of the present invention for the manufacture of a medicament for repairing biological tissue.

The present invention also relates to a composition of the present invention or a hydrogel of the present invention when used in a method of repairing biological tissue.

The present invention also relates to a composition having an active ingredient for use in repairing biological tissue, wherein the active ingredient is a hydrogel of the present invention.

The present invention also relates to the use of a composition of the present invention or a hydrogel of the present invention in repairing biological tissue, such as described above.

In one embodiment, the biological tissue is cartilage. Preferably, the cartilage is articular cartilage.

The term "therapeutically-effective amount", as used herein, refers to an amount of the hydrogel of the present invention that is sufficient to treat, alleviate, ameliorate, relieve, delay onset of, inhibit progression of, reduce severity of, and/or reduce incidence of one or more symptoms or features of the disease, disorder, and/or condition. In particular, a "therapeutically-effective amount" is an amount sufficient to repair biological tissue, such as cartilage (and in particular articular cartilage). The term "repair" refers to the replacement or restoration of damaged biological tissue, preferably such that the original functionality of the damaged tissue is restored. A person skilled in the art will understand that the restoration may be complete, such that 100% of the original functionality has been restored, or may be partial, such that only a portion of the original functionality has been restored.

The hydrogels of the present invention may be administered using any amount and any route of administration effective for treatment. The exact amount required will vary from subject to subject, depending on the species, age, and general condition of the subject, the severity of the infection, the particular hydrogel, its mode of administration, its mode of activity, and the like.

Compositions and hydrogels of the present invention are typically formulated in dosage unit form for ease of administration and uniformity of dosage. It will be understood, however, that the total daily usage of the hydrogels and/or hydrogel assemblies of the present invention will be decided by the attending physician within the scope of sound medical judgment.

The specific therapeutically effective dose level for any particular subject or organism will depend upon a variety of factors including the disorder being treated and the severity of the disorder; the activity of the specific active ingredient employed; the specific polymer and/or cells employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The hydrogels of the present invention may be administered by any route. In some embodiments, the hydrogels of the present invention are administered by a variety of routes, including direct administration to an affected site. For example, hydrogels may be administered locally near a site which is in need of tissue regeneration. Local administration may be achieved via injection of the cooled hydrogel directly to a site in need of tissue regrowth and/or repair.

In certain embodiments, the hydrogels of the present invention may be administered such that encapsulated cells and/or therapeutic agents to be delivered are released at concentrations ranging from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered, for example, three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

In some embodiments, the present invention encompasses "therapeutic cocktails" comprising the hydrogels of the present invention. In some embodiments, hydrogels comprise a single cell type and, optionally, a therapeutic agent. In some embodiments, hydrogels comprise multiple different cell types and, optionally, a therapeutic agent.

It will be appreciated that cell-laden hydrogels in accordance with the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, a hydrogel comprising a certain cell type to be used to promote tissue growth may be administered concurrently with another therapeutic agent used to stimulate growth of the same tissue), or they may achieve different effects (e.g., control of any adverse effects, such as inflammation, infection, etc).

E. Kits

The invention provides a variety of kits comprising one or more of the hydrogels and/or compositions of the present invention. For example, the invention provides a kit comprising a hydrogel and/or composition and instructions for use. A kit may comprise multiple different hydrogels and/or compositions. A kit may optionally comprise polymers, cells, ECMPs, biologically-active compounds, and the like. A kit may comprise any of a number of additional components or reagents in any combination. All of the various combinations are not set forth explicitly but each combination is included in the scope of the invention. A few exemplary kits that are provided in accordance with the present invention are described in the following paragraphs.

According to certain embodiments of the invention, a kit may include, for example, (i) a solution comprising a polymer, a solution comprising ECMP; and (ii) instructions for forming a hydrogel from the solution.

According to another embodiment, a kit may include, for example, (i) a composition comprising a polymer and ECMP; and (ii) instructions for forming a hydrogel from the composition.

Kits may further include other materials desirable from a commercial and user standpoint, including other buffers, diluents, filters, needles, and syringes.

Kits typically include instructions for use of the hydrogels of the present invention. Instructions may, for example, comprise protocols and/or describe conditions for production of hydrogels, administration of hydrogels to a subject in need thereof, production of hydrogel assemblies, etc. Kits will generally include one or more vessels or containers so that some or all of the individual components and reagents may be separately housed. Kits may also include a means for enclosing individual containers in relatively close confinement for commercial sale, e.g., a plastic box, in which instructions, packaging materials such as styrofoam, etc, may be enclosed.

The kit or "article of manufacture" may comprise a container and a label or package insert on or associated with the container. Suitable containers include, for example, bottles, vials, syringes, blister packs, etc. The containers may be formed from a variety of materials such as glass or plastic. The container holds the hydrogel or composition which is effective for treating the condition and may have a sterile access port (for example the container may be an intravenous solution bag or a vial having a stopper pierceable by a hypodermic injection needle). The label or package insert indicates that the hydrogel or composition is used for treating the condition of choice. In one embodiment, the label or package insert includes instructions for use and indicates that the therapeutic composition can be used to repair or regenerate tissue.

The present invention will now be more fully described with reference to the accompanying examples and drawings. It should be understood, however, that the description following is illustrative only and should not be taken in any way as a restriction on the generality of the invention described above.

EXAMPLES

Materials

Chemicals were purchased from Sigma-Aldrich unless otherwise stated. Stannous 2-ethylhexanoate ($Sn(OCt)_2$), N-isopropylacrylamide (NIPAAm), 2-hydroxyethyl methacrylate (HEMA), 4,4'-azobis(4-cyanovaleric acid) (ACVA) and N-acryloxysuccinimide (NAS) were used as received. Oligo(ethylene glycol) monomethyl ether methacrylate (OEGMA, $M_n$=475) was purified by passing its solution in dichloromethane (with 1:1 volume ratio) through a neutral alumina column to remove the inhibitor prior to use. D,L-lactide (LA) monomer was dried under vacuum at 40° C. for 24 h prior to use. Azobisisobutyronitrile (AIBN) was kindly gifted by School of Chemistry in University of Sydney.

Synthesis of HEMA-poly(lactide) (HEMA-PLA) macromonomer

HEMA-PLA macromonomer was synthesized by ring-opening polymerization of LA with the hydroxyl group of HEMA as the initiator and $Sn(OCt)_2$ as the catalyst (Scheme 1).[6]

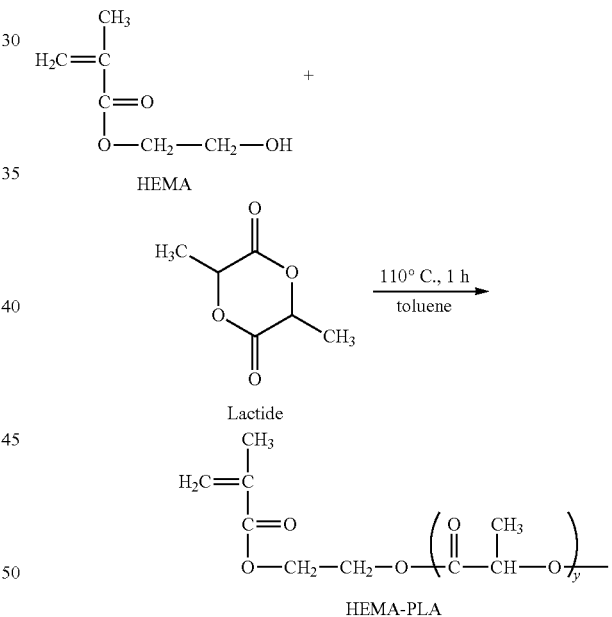

Scheme 1. Synthesis of HEMA-PLA macromonomer

LA and HEMA were mixed in a three-neck flask at 110° C. under a nitrogen atmosphere for 15 min. Subsequently, a mixture of 1 mol % of $Sn(OCt)_2$ (with respect to the HEMA feed) in 1 mL of anhydrous toluene was added to the LA/HEMA solution. The resulting mixture was stirred at 300 rpm and 110° C. for 1 h under a nitrogen atmosphere. After the reaction, the mixture was dissolved in tetrahydrofuran and precipitated in cold distilled water at 1° C. The formed precipitate was separated by centrifugation at 3000 rpm for 5 min. The centrifugation cycle was repeated three times to remove all unreacted monomers and by-products (mainly salts). The precipitate was then dissolved in ethyl acetate. The suspended solid particles were removed from the solution with centrifugation at 6000 rpm for 5 min and the supernatant was dried with MgSO₄ for 12 hr. The dried supernatant was filtered to remove the MgSO₄ particles. The polymeric solution was then dried at 60° C. under reduced pressure and the residue of solvent was further removed under vacuum at 40° C. for 24 hr. The resultant viscous oil was stored in a fridge for further use.

The feed ratio of HEMA:LA was varied from 1:1.5 and 1:2.5 to obtain PLA/HEMA macromer with different lactate lengths. Two PLA/HEMA macromonomers with lactate lengths of 3 and 6 were synthesized by using 1:1.5 and 1:2.5 mol ratio of HEMA to LA monomers, respectively.

The synthesis of PLA/HEMA macromer was confirmed, using $^1$H NMR spectra with evidence of proton peaks from both HEMA and LA. The molar ratio of LA to HEMA in PLA/HEMA macromer was calculated from $^1$H NMR spectra using the peaks at 5.2 ppm for methine in lactate, and total integrations at 5.7 ppm and 6.0 ppm peaks for HEMA.

Synthesis of poly(NIPAAm-co-NAS-co-(HEMA-PLA)-co-OEGMA) (PNPHO)

PNPHO was synthesised using either method (1) or (2) as described below (Scheme 2).

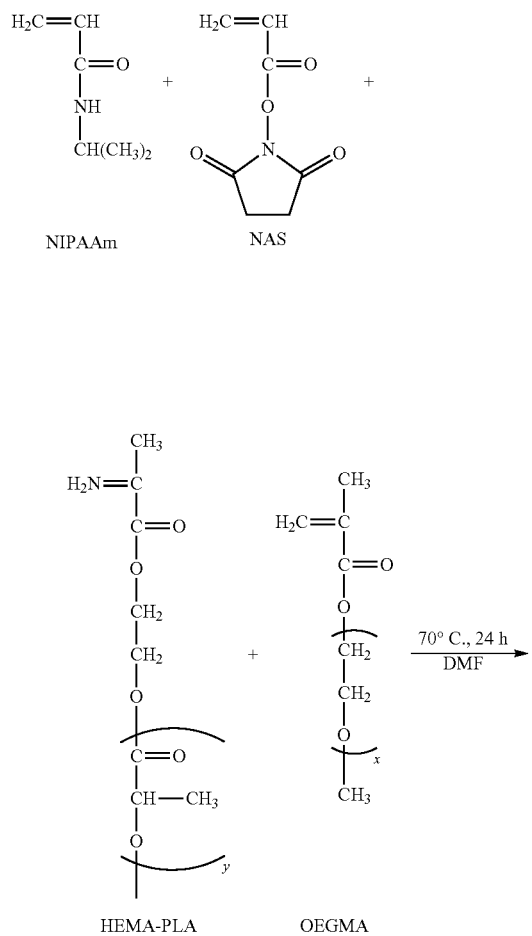

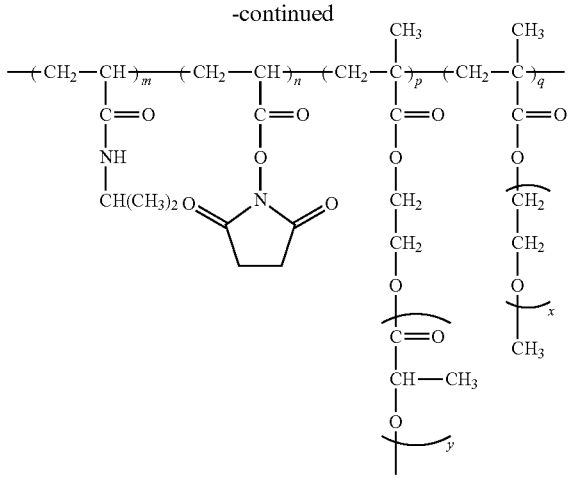

P(NIPAAm-co-NAS-co-(HEMA-PLA)-co-OEGMA)

Method 1

PNPHO was synthesized by free radical polymerization using AIBN as the initiator. A Schlenk flask with a magnetic stir bar and a rubber septum was charged with NIPAAm (12 mmol), NAS (1.0 mmol), HEMA-PLA (0.57 mmol), OEGMA (0.56 mmol), AIBN (0.07 mmol) and anhydrous N,N'-dimethylformamide (DMF). The flask was deoxygenated by three freeze-pump-thaw cycles, and then sealed followed by immersing the flask into an oil bath preheated at 70° C. to start the polymerisation. After reaction for 24 h, the reaction mixture was cooled to room temperature, precipitated in diethyl ether, filtered, and then dried under vacuum. The polymer was purified twice by redissolving/re-precipitating with THF/ethyl ether and finally dried under vacuum for 2 days.

Method 2

PNPHO was synthesized by free radical polymerization, using ACVA as the initiator. Composition of copolymer was changed by varying the lactate length (3 and 6 in HEMA-PLA), molar ratios of HEMA-PLA (6, 8, and 11 mol %) and OEGMA (3, 5, and 8 mol %). Known amounts of NIPAAm, NAS, HEMA-PLA, OEGMA, ACVA (7.0×10⁻⁵ mol) were dissolved in 13 mL anhydrous N,N'-dimethylformamide in a round bottom, one neck flask. The system was then deoxygenated by at least three freeze-pump-thaw cycles, using liquid nitrogen as the coolant. Our results also showed that it is feasible to deoxygenate the monomer solution by purging nitrogen gas for 10 min in the solution under vacuum. This technique provides a more efficient method to remove oxygen from solution in large scales. The reactor was then sealed and immersed in an oil bath at 70° C. for 24 h. The resultant polymeric solution was then cooled at room temperature for 1 hr and precipitated in 250 mL diethyl ether. The precipitate was then collected by filtering the suspension and dried under vacuum for 6 hr. The dried powder was dissolved in tetrahydrofuran and precipitated in diethyl ether to further remove residues of macromers. The final powder was dried under vacuum for at least 48 h.

PNPHO Compositions

Figure 2:
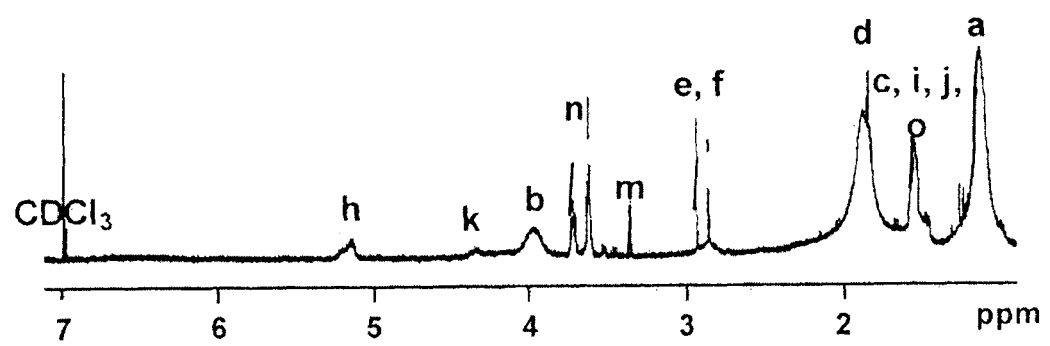
FIG. 2. $^1$H NMR spectrum of PNPHO.

The synthesis of PNPHO copolymers was confirmed with $^1$H NMR spectra with evidence of proton peaks for each monomer, as shown in FIG. 2. Characteristic proton peaks were detected for NIPAAm (a and b), NAS (e), HEMA-PLA (f, h, k), and OEGMA (m and n). The final composition of copolymer was calculated based on the integration of these peaks from each monomer as for NIPAAm (a), NAS(e/2-f), HEMA-PLA (h), and OEGMA (n/2). The molecular weights of copolymers were measured using gel permeation chromatography. For each composition, at least three syntheses were conducted and the variance between feed ratios and the final composition of copolymers were statistically analyzed, using one way Analysis of Variance (ANOVA). The compositions of copolymers were found to be consistent ($p>0.05$) with the feed ratios, as reported in Table 1. In this study copolymer is denoted as PNPHO and the subscript is added that corresponds to HEMA-PLA (lactate length) to OEGMA molar ratios. For example $PNPHO_{8(6)3}$ stands for the copolymer synthesized with 8 mol % HEMA-PLA with lactate length of 6, and 3 mol % OEGMA.

TABLE 1

Feed ratio, final composition and molecular weight of PNPHO synthesized with different compositions.

| Monomers molar ratio[1] | Final composition of copolymer[1] | Mw |
| --- | --- | --- |
| 6(3)/3/7/84 | 8.7(3)/3.4/7.9/80 | 21,212 |
| 8(3)/3/7182 | 10.9(3)/3.9/8.2/77 | 21,451 |
| 11(3)/3/7/79 | 11(3)/3/8/78 | 22,444 |
| 6(3)/5/7/82 | 7.8(6)/5/8.2/79 | 22,551 |
| 8(3)/5/7/80 | 9.1(6)/6.5/8.4/76 | 23,544 |
| 11(3)/5/7/77 | 9.1(6)/7/7.9/76 | 23,001 |
| 6(3)/8/7/79 | 8.2(6)/7/7/77.8 | 25,541 |
| 8(3)/8/7/77 | 8.8(6)/8.1/8.1/75 | 25,550 |
| 11(3)/8/7/74 | 11.8(6)/8/8.2/72 | 27,002 |
| 6(6)/3/7/84 | 6.8(6)/3/8.5/81.5 | 23,211 |
| 8(6)/3/7/82 | 9.1(6)/3/8/79.9 | 22,551 |
| 11(6)/3/7/79 | 12.2(6)/3.2/8.6/76 | 24,555 |
| 6(6)/5/7/82 | 6(6)/5.6/8.4/80 | 27,521 |
| 8(6)/5/7/80 | 6(6)/8.1/5.5/8.4/77 | 25,521 |
| 11(6)/5/7/77 | 11.1(6)/5.6/8/75.3 | 26,555 |
| 6(6)/8/7/79 | 9(6)/8.5/8/74.5 | 28,452 |
| 8(6)/8/7/77 | 10(6)/9/8.3/72.6 | 28,881 |
| 11(6)/8/7/74 | 11(6)/8/7/74 | 27,885 |

[1]PLA-HEMA(lactate length):OEGMA:NAS:NIPAAm

In the synthesis and purification of HEMA-PLA, OEGAMA and PNPHO different organic solvents were used, including ethyl acetate, dimethylformamide, tetrahydrofuran, and diethyl ether. Gas chromatography was used to measure the residues of these solvents in PNPHO. The results showed that the concentration of all these organic solvents in the final products was below ppm level, showing that the multiple step purification process was efficient and in vivo and in vitro applications of this polymer precursor are safe.

Solubility of PNPHO in PBS

The monomer ratios of PNPHO were modified to acquire a range of compositions that were dissolved in aqueous media, such as PBS for the development of injectable formulations. NIPAAm-based copolymers are soluble in aqueous solutions below their LCST due to the formation of hydrogen bonds between the copolymer polar groups and water molecules. In this study the effects of lactate length, HEMA-PLA and OEGMA contents on the solubility of PNPHO were studied by measuring the saturation concentration of different compositions of PNPHO in PBS.

Figure 3:
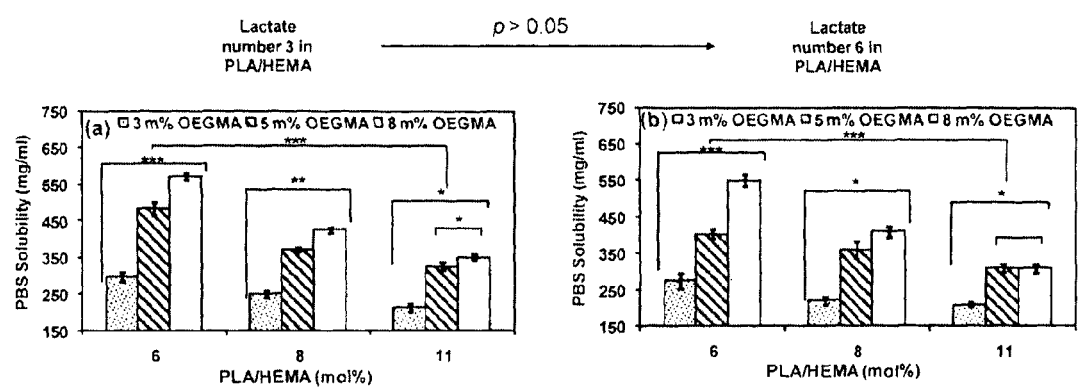
FIG. 3. Solubility of copolymers synthesized at different mole fraction of HEMA-PLA in aqueous solution at 4° C. for lactate number of 3 (a) and 6 (b), (*, , and * represent p<0.05, <0.01, and <0.001, respectively).

The results in FIG. 3 demonstrate that increasing lactate length within the range of 3 to 6 in the HEMA-PLA backbone had no significant impact on the solubility of PNPHO in PBS ($p>0.05$). Hydrophobic properties of a side chain in the backbone of PNPHO therefore had minimal impact on overall solubility of PNPHO in aqueous media, within the range examined. Therefore, by changing the lactate length, other characteristics of PNPHO, such as gelling behavior and mechanical properties, can be tuned without affecting the solubility of PNPHO in an aqueous media.

The solubility of PNPHO in PBS can be tuned by changing both hydrophobic and hydrophilic contents. The PLA segment is the main hydrophobic backbone, while both NAS and HEMA monomers exhibit relatively limited hydrophilic properties. OEGMA was therefore included in the synthesis of PNPHO to promote the hydrophilic properties of the copolymer. Increasing HEMA-PLA (i.e. the hydrophobic content) in copolymers from 6 to 8 and 11 mol % decreased the solubility of PNPHO in PBS by 30% and 50%, respectively. For example, saturation concentration of $PNPHO_{6(6)3}$ was significantly ($p<0.001$) decreased from 250±17 mg/mL to 190±10 mg/mL and 164±6 mg/mL in $PNPHO_{3(6)3}$ and $PNPHO_{11(6)3}$, respectively. This solubility reduction was also due to decreasing the concentration of the relatively hydrophilic segment NIPAAm in the copolymer ($p<0.05$). Therefore, decreasing NIPAAm content in PNPHO substantially affected the hydration of the copolymer.

The solubility of PNPHO in water was increased dramatically, when using more than 3 mol % (e.g. 1.5 mol %) OEGMA as a hydrophilic segment. Results showed that copolymers with OEGMA contents of less than 3 mol % were not soluble in aqueous media. The results in FIG. 3 show that the solubility of PNPHO copolymers with 6 mol % PLA/HEMA was significantly increased 2- and 3-fold when elevating the OEGMA concentration from 3 mol % to 5 and 8 mol %, respectively. However, in copolymers that contained a higher molar ratio of hydrophobic segment HEMA-PLA (i.e. 8 mol % and 11 mol %), OEGMA concentration had little effect on the solubility of PNPHO. This behavior was attributed to formation of copolymers with longer chains and higher MW, which impeded the hydration and solubility of the copolymer in aqueous solution. As an illustration, the molecular weight of $PNPHO_{11(3)8}$ was significantly ($p<0.01$) higher than $PNPHO_{11(3)5}$ (27K compared to 26K), which compromised the effect of its higher hydrophilic content, and therefore the saturation concentration for both compounds was approximately 300 mg/mL.

The effect of concentration of water soluble PNPHO copolymers on the injectability of their solutions through an 18 G needle was assessed. It was found that 150 mg/ml PNPHO solution in PBS was injectable through 18 G needle and this concentration of copolymer was used for further analysis. Higher concentrations of polymers can be used for other biomedical applications such as scaffold fabrication for in vitro tissue growth.

Conjugation of PNPHO with Naturally Derived Proteins and Formation of Hydrogels

The presence of the succinimide ester group in the molecular structure of PNPHO provided facial active sites for conjugation with naturally derived proteins such as elastin, collagen, and recombinant tropoelastin. Different conjugation techniques (as shown in FIG. 1) were used to prepare protein-copolymer hydrogels.

Elastin

In method (a), PNPHO copolymer was dissolved in PBS for 24 hr. Protein solution was added to PNPHO solution and incubated at 4° C. for another 24 hr. In method (b), dissolution of PNPHO and protein conjugation were conducted at the same time. In method (c), PNPHO was dissolved and conjugated with naturally derived protein on a shaker. In method (d), PNPHO-protein conjugate powder was formed by freeze drying PNPHO-protein solution. The conjugate powder was dissolved in PBS on a shaker to form the final polymeric solution: The protein-PNPHO solutions formed with different techniques were converted to hydrogels by increasing the temperature to 37° C.

Figure 4:
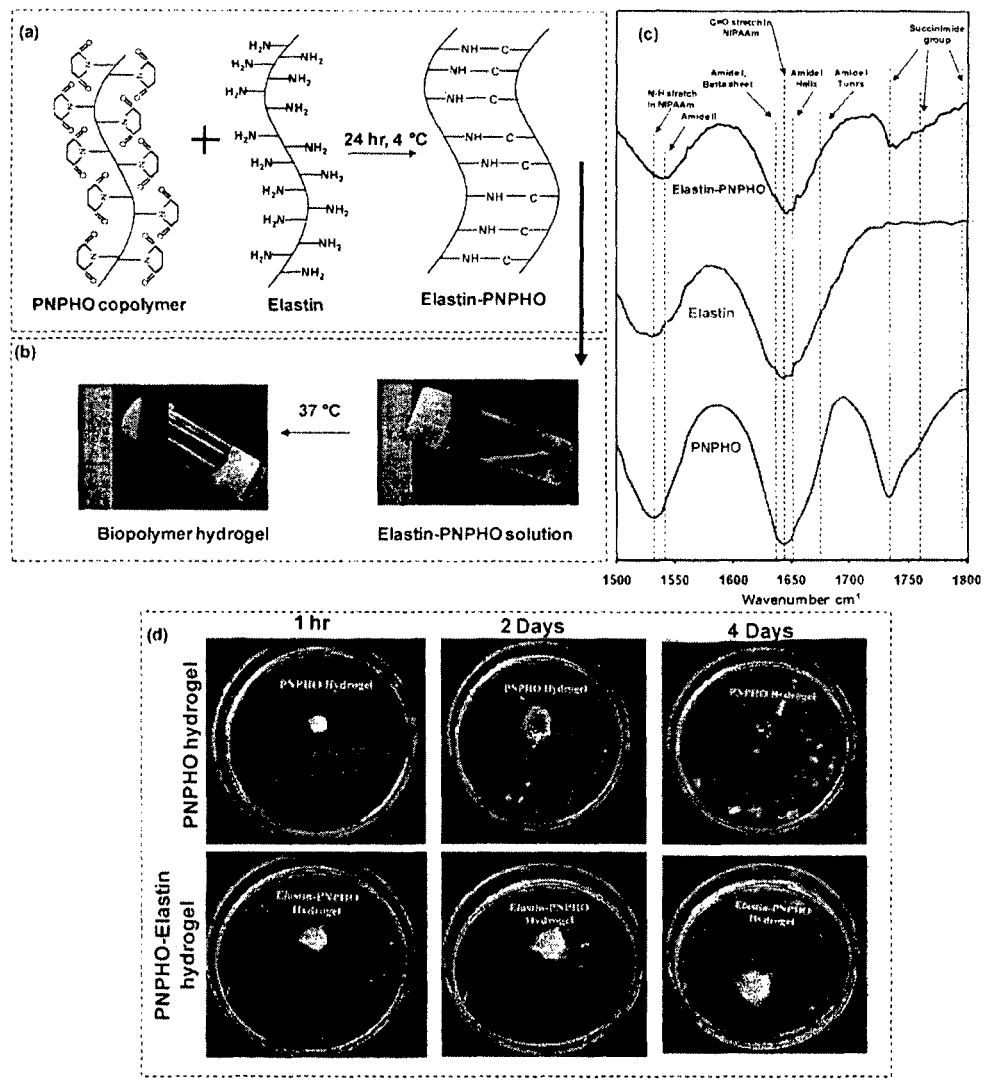
FIG. 4. Bioconjugation of elastin and PNPHO copolymer in PBS (a), biopolymer hydrogel formation at 37° C. (b), FTIR spectra of PNPHO copolymer and biopolymer hydrogel (c) and stability test of PNPHO and elastin-PNPHO hydrogels in physiological environment (d).

The feasibility of conjugating or crosslinking this class of copolymers with naturally derived protein was examined. For this purposes of study, PNPHO$_{6(6)8}$ and elastin (as a model protein) were used. The schematic of the procedure, used for the conjugation of PNPHO with elastin, is shown in FIG. 4(a). In each run a 100 mg/mL elastin and 150 mg/mL of PNPHO were used to form elastin-copolymer conjugate. In this study, different techniques (as schematically shown in FIG. 1) were used to decrease the preparation time of protein-copolymer solution to ease the clinical application of this system. The chemical conjugation of elastin and PNPHO with different techniques was confirmed by measuring the retention rate of elastin within the structure of the conjugated hydrogel. Previous studies showed that after 24 hr of incubation, less than 40 wt % of proteins were retained in the structure of hydrogels.[7] In this study, the conjugation ratio of elastin and PNPHO was correlated to the retention ratio of elastin in biopolymer structure after 24 hr of thorough washing of the conjugate hydrogel in PBS at physiological conditions. The Bradford protein assay was used to determine the concentration of solubilized protein in the washing media.[8]

The preparation time and elastin retention ratio in conjugated hydrogels, prepared with different techniques, are summarized in Table 2.

TABLE 2

The effect of preparation method on elastin retention

| Preparation technique[1] | Preparation time | Elastin Retention (wt %) |
|---|---|---|
| Method a | 48 hours | 51 ± 4 |
| Method b | 24 hours | 78 ± 3 |
| Method c | 10 hours | 77 ± 3 |
| Method d | 6 hours | |

[1]Please refer to FIG. 1 for schematic overview of preparation techniques.

As mentioned above, in method (a) PNPHO was dissolved in PBS within 24 hrs. Elastin solution was subsequently added to the PNPHO solution and incubated at 4° C. for another 24 hrs. Bradford protein assay results showed that 51±4 wt % of elastin participated in the chemical conjugation reaction. By simultaneous dissolution and conjugation of PNPHO copolymer and elastin (method (b)) the preparation time was decreased from 48 hr to 24 hr and the elastin retention ratio was significantly (p<0.05) increased to 78±3 wt %. The preparation time was further decreased to 10 hr in method (c) by conducting the dissolution and conjugated phase at 4° C. under shaker without affecting the elastin retention ratio (p>0.05). In method (d), protein (such as elastin) and copolymer were conjugated. The conjugate solution was then freeze dried, forming elastin-PNPHO powder. This powder was dissolved in PBS in 6 hr and can be delivered as the final product. The preparation time was decreased from 48 hr to 6 hr, which has been deemed to be a clinically acceptable preparation time. Method (d) was used for the preparation of different protein-PNPHO hydrogels.

The structure of the thermally responsive PNPHO copolymer consists of hydrophilic amide bonds and hydrophobic isopropyl groups. Increasing the temperature of solutions (in both PNPHO and elastin-PNPHO solutions) from 4° C. to 37° C. (above the LCST) instigated the dehydration of hydrophobic isopropyl groups during the coil-to-globe transition (driven by PNIPAAm content), followed by precipitation of the compounds. There is a strong hydrogen bond between water and both proteins and copolymer, which resulted in formation of a conjugate hydrogel at above LSCT, as shown in FIG. 4(b).

ATR-FTIR was used to confirm the formation of covalent bonds between elastin and PNPHO. The results in FIG. 4(c) show that the key peaks for PNPHO include N–H and C=O stretches from NIPAAm at 1540 cm$^{-1}$, and 1645 cm$^{-1}$ and three characteristic peaks from succinimide ester group at 1740 cm$^{-1}$, 1763 cm$^{-1}$, and 1795 cm$^{-1}$. The absence of these peaks for NAS in ATR-FTIR spectra of elastin-copolymer conjugate underlined that elastin was covalently bonded to the succinimide ester group in PNPHO.

The presence of elastin within the structure of the conjugate hydrogel was also confirmed by the characteristic ATR-FTIR peaks of elastin. In general for all proteins such as elastin, the amide bonds are presented within 1600 cm$^{-1}$ to 1700 cm$^{-1}$. This region is from the C=O stretching vibration and confirms the secondary structure of the protein backbone. The peaks between 1600 cm$^{-1}$ and 1640 cm$^{-1}$ correspond to the intermolecular interaction and beta-sheet bands. The elastin-PNPHO hydrogel exhibited a peak at 1640 cm$^{-1}$, confirming the presence of intermolecular interaction and formation of stable protein structure. In addition, the peaks between 1640 cm$^1$ and 1660 cm$^{-1}$ demonstrate the contribution from random coils and alpha-helices in elastin. The conjugated copolymer-elastin also exhibited a peak at 1640 cm$^{-1}$ due to the presence of α-helices in elastin. The remaining peaks in Amide I region from 1660 cm$^{-1}$ to 1690 cm$^{-1}$ dominated by vibrations from beta-turn structures, with some small peaks from other structures, denoted as turn points. In amide II region (1500 to 1600 cm$^{-1}$), the ATR-FTIR spectra of elastin-PNPHO exhibited a significant shift corresponded to N–H stretching of NIPAAm and elastin from 1535 cm$^{-1}$ to 1545 cm$^{-1}$ wavenumber. This shift in FTIR spectra confirms the molecular interaction between PNPHO and elastin in the elastin-copolymer conjugated product.

Figure 5:
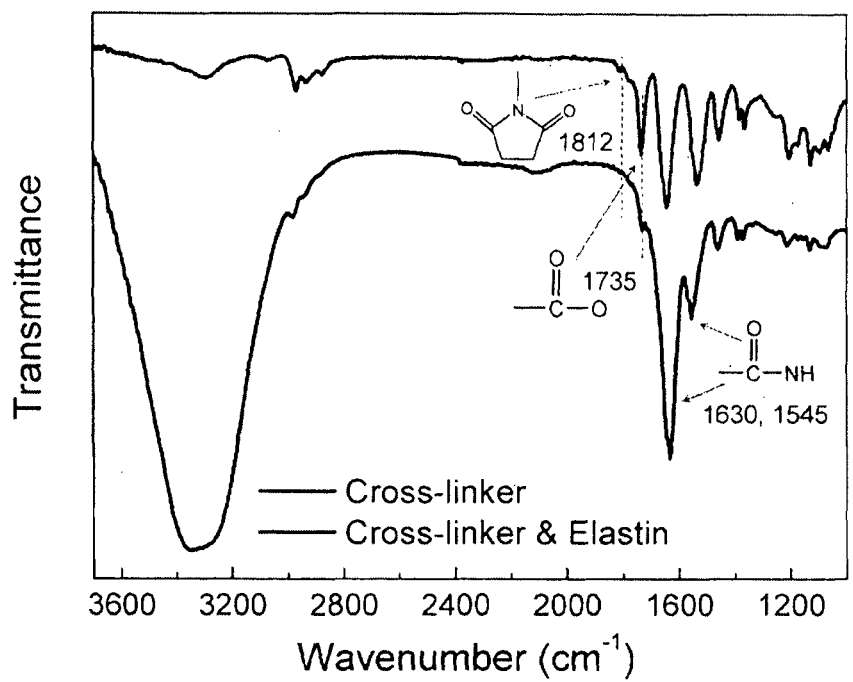
FIG. 5. ATR-FTIR spectra of polymer (red) and hydrogel (black)

In addition, as shown in FIG. 5, the polymer exhibited a characteristic peak at 1812 cm$^{-1}$ associated with the succinimide group. After the conjugation of elastin, this peak disappeared completely, indicating the participation of elastin in the condensation reaction with the succinimide group. Upon comparison of spectra before and after incorporation of elastin, a significant attenuation of ester group absorption (1735 cm$^{-1}$) and a dramatic increase of amide group absorption (1630 and 1545 cm$^{-1}$) was observed, which resulted from the conversion of the ester bond to an amide linkage in the course of the crosslinking. This resulted in the observed corresponding relative intensity variation of these characteristic peaks.

In the absence of protein, PNPHO was precipitated in PNPHO solution at 37° C. and random entanglement of polymer chains formed a fragile hydrogel with a poor physical integrity. The PNPHO hydrogel was fully dissolved in PBS after 4 days in PBS (which was used to mimic the physiological environment) as shown in FIG. 4(c). Conjugation of PNPHO with protein (e.g. elastin) led to formation of covalent bonds that maintained the integrity of the hydrogel for a longer period of time. This chemical conjugation therefore provides sufficient stability to hydrogels for different biomedical applications.

The results of visual observation, intermolecular interaction acquired from ATR-FTIR analysis, and protein retention rate in conjugate hydrogels demonstrated that the synthesized copolymer has the capacity to covalently bind to a protein such as elastin. The physico-chemical characteristics of elastin-PNPHO conjugates formed with different compositions of copolymer were studied to select the composition suitable for injection and biomedical application. These analyses included gelling properties, conjugation efficiency and degradation behaviour.

Collagen

Since the succinimide linker exhibits high reactivity and optimized accessibility towards compounds containing amino groups, it is reasonable to postulate that the polymer can be applied to other types of natural polymers with amino groups for the fabrication of injectable hydrogels. To confirm this assumption the feasibility of a reaction between the polymer and collagen was examined.

A collagen solution (OVICOLL®CLEAR, 1%, pH 2.5-3.5) was neutralized with small aliquots of 1 M NaOH solution. 250 µL of the resulting neutralized collagen solution was thoroughly mixed with 500 µL of 250 mg/1 mL polymer/PBS solution. The mixture was then transferred to a refrigerator. After preservation at 4° C. for 24 h, the mixture was then allowed to gel at 37° C. followed by washing with distilled water to remove any impurities.

Figure 6:
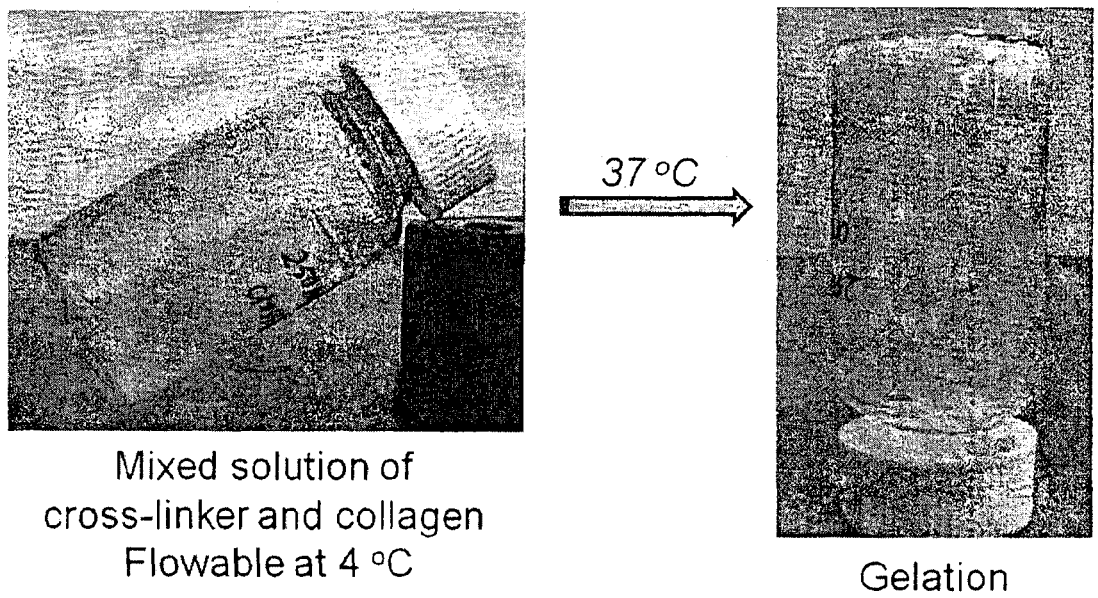
FIG. 6. Macroscopic image of the hydrogel (polymer and collagen) formed at 37° C.

The results (FIG. 6) show the successful formation of hydrogel.

Gelling Behaviour

In this study, the effects of LA molar ratio, OEGMA and HEMA-PLA content on the gelation behaviour of elastin-copolymer conjugates were studied. The gelation temperature and, gelation time were measured for the conjugation of elastin with different types of PNPHO synthesized herein.

Gelling Temperature

Figure 7:
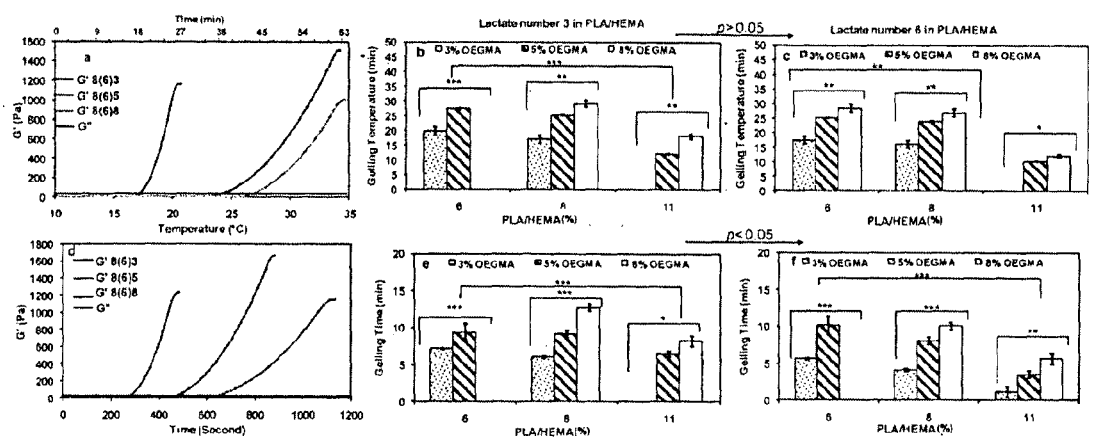
FIG. 7. Effect of temperature on elastic modulus of different composition of copolymer (a) elastic modulus of different copolymer composition over time at 37° C. (e). Gelling temperature ((b) and (c)) and gelling time ((e) and (f)) of different compositions of copolymer synthesized with lactate numbers of 3 ((b) and (e)) and 6 in HEMA-PLA ((c) and (f)).

Rheological behaviors of elastin conjugated with different types of PNPHO copolymer were assessed within the temperature range of 10° C. to 37° C. at the rate of 0.3° C./min. This data was used to determine the gelling temperature of elastin-PNPHO solutions, formed with different compositions of copolymer. The rheological behavior of three compositions of copolymers is shown as an example in FIG. 7($a$). Below the LCST, all these three elastin-PNPHO solutions were maintained in liquid phase. Increasing the temperature above the LOST triggered the dehydration phase, followed by hydrogel formation. Based on rheological behavior of conjugates, the gelling temperature was recorded at the crossover point of dynamic storage (G') and loss modulus (G"), as shown in FIG. 7($a$). After this point, the elastic response of hydrogels dominated the viscous response and the structure of the hydrogel continued to evolve, as G' increased. At this period the G" remained constant at approximately 1 Pa. Results in FIG. 7($b$) showed that most of the examined elastin-copolymer solutions enabled the formation of a hydrogel below 37° C. (body temperature). However, the LCST for the elastin-PNPHO$_{6(3)8}$ conjugate solution was approximately 40° C. i.e. above body temperature. Therefore, this composition of copolymer may not be a favourable candidate for biomedical applications. The high LCST in PNPHO$_{6(3)8}$ was due to high hydrophilic to hydrophobic content ratio in this copolymer. Moreover, in PNPHO$_{11(3)3}$ and PNPHO$_{11(6)3}$ lack of hydrophilic sites inhibited the rehydration of biopolymer after condensation phase. This effect led to precipitation of conjugate in the powder form with weak structural integrity. The effect of lactate, OEGMA and HEMA-PLA molar ratio on gelling temperature of different conjugates is presented in FIGS. 7($b$) and ($c$).

These data show that lactate molar ratio in HEMA-PLA macromer had no significant impact on the gelling temperature ($p>0.05$). A similar trend was also observed for the effect of this parameter on solubility presented in FIG. 3. This result suggests that the hydrophobic properties of side chains in the HEMA-PLA backbone of the copolymer had no significant effect on the hydrophilic properties of the copolymer within the range examined.

The presence of OEGMA played an important role in the gelation behaviour of conjugated solutions. The gelling temperature of the elastin-PNPHO conjugate was elevated from 17±2° C. to 24±1° C. and 27±2° C. when increasing OEGMA content from 3 mol % (PNPHO$_{8(6)3}$) to 5 (PNPHO$_{8(6)5}$) and 8 mol % (PNPHO$_{8(6)8}$), respectively ($p<0.01$).

The effect of HEMA-PLA concentration as a hydrophobic segment on gelling temperature of the PNPHO copolymer was also studied. Increasing the HEMA-PLA content from 6 mol % to 8 mol % and 11 mol % significantly ($p<0.001$) decreased the gelling temperature of conjugated copolymer by approximately 20% and 30%, respectively. These data demonstrate that the gelling temperature of protein-PNPHO conjugated is tunable within the range of 11° C. to 40° C. by manipulating the hydrophobic and hydrophilic contents.

Gelling Time

Rheological behaviours of conjugated solutions were examined at 37° C. over time to determine the gelling time of elastin-PNPHO solutions with different compositions of copolymer. The rheological behaviour of three compositions of copolymers is shown as an example in FIG. 7($d$). Gelation time is important for in vivo applications of injectable formulations. Rapid gelation may lead to premature gelation and needle blockage or increase the viscosity of injectable solutions. Both of these issues result in an inconvenient administration of formulation. A gelling time of about 9 minutes was considered optimal for clinical operation. The gelling time of the protein-PNPHO solution was altered by changing lactate length, HEMA-PLA and OEGMA contents, as shown in FIGS. 7($e$) and ($f$).

Increasing the lactate length from 3 to 6 significantly ($p<0.05$) decreased the gelling time of the conjugated system by approximately 10%. By elevating HEMA-PLA content from 6 mol % to 8 mol % and 11 mol %, the gelling time was reduced by 20% and 40%, respectively. These reductions in gelling time were attributed to elevation of the hydrophobic fraction and the molecular weight of the PNPHO copolymer. The former accelerated the condensation rate of elastin-PNPHO solution, while the latter affected the entanglement of the polymer chain during the gelation phase, hence the gelation time.

Increasing OEGMA content from 3 mol % to 5 mol % and 8 mol % resulted in significant ($p<0.001$) elevation of gelation time from 2- to 3-fold, respectively. Increasing OEGMA content was an obstacle for the hydrophobic interactions during the condensation and therefore the hydrogel formation. For example, the rheological behaviour of PNPHO$_{8(6)3}$, PNPHO$_{8(6)5}$, and PNPHO$_{8(6)8}$, shown in FIG. 7($d$), revealed that the copolymer with higher hydrophilic content exhibited shorter gelation time. In PNPHO$_{8(6)3}$ the gelation time was 7.2±0.5 min, which was lower than for PNPHO$_{8(6)5}$ (10.1±0.6 min) and PNPHO$_{8(6)8}$ (12.2±0.2 min). The data acquired here demonstrate that it is viable to change the gelling temperature and time of conjugated solutions by varying the composition of the copolymer. This allows the gelling behaviour of conjugate system to be tuned based on the final biomedical application of injectable hydrogel.

Conjugation Efficiency of PNPHO

The PNPHO copolymer was designed for conjugation to protein based biopolymers with potential application in delivery of encapsulated biofactors to the required site and in vivo tissue regeneration. It may be viable to use this concept for conjugating of a therapeutic protein to PNPHO copolymer for injectable administrations and controlled release. For in vivo tissue engineering, incorporation of naturally derived protein within the structure of copolymer enhances the biological activity of the synthetic copolymer. The conjugation capacity of different compositions of copolymers was assessed by evaluating the retention ratio of elastin within the structure of the copolymer. For this analysis, the Bradford technique was used. The effects of lactate length, HEMA-PLA and OEGMA contents on conjugation capacity of copolymers were assessed.

It was found that elastin conjugation to copolymers was promoted when nearly equimolar ratios of hydrophilic to hydrophobic segments were used. For copolymers with lactate number of 6, elastin conjugation approached to 91±1 wt % for copolymer that possessed (8 mol %) OEGMA/(8 mol ° A)) HEMA-PLA (i.e. equimolar ratio). In copolymers synthesized with lactate number of 3 (relatively lower hydrophobic properties of the HEMA-PLA backbone), the highest elastin conjugation of 81±2 wt % was achieved for HEMA-PLA and OEGMA contents of 11 mol % and 8 mol %, respectively.

The results of the Bradford protein assay demonstrate that elastin conjugation was more than 65 wt % and up to 90%. The conjugation capacity of PNPHO copolymer is superior to previous synthesized copolymers for conjugation to proteins. The high stability of conjugated elastin in the structure of PNPHO may be attributed to the formation of covalent bonds between elastin and the copolymer, as confirmed by FTIR results (discussed above). In biomedical applications of injectable hydrogels, it is important to be able to incorporate high ratio of protein within a copolymer at the molecular level. The copolymer compositions selected for further characterization are $PNPHO_{11(3)5}$, $PNPHO_{11(3)8}$, $PHPHO_{8(6)5}$, and $PNPHO_{8(6)8}$, which all displayed conjugation efficiency above 80 wt %.

Biresorbable Behaviour of Protein-PNPHO Hydrogels

In tissue engineering, it is favourable to use a polymeric structure that is biodegradable or bioresorbable in biological conditions. PNPHO was designed with degradable hydrophobic domain (HEMA-PLA)—its gradual cleavage along with the retention of hydrophilic backbone (OEGMA) from the copolymer molecular structure may lead to dissolution of hydrogel in physiological environment. In addition, the rate of bioresorption is an important factor in the utility of hydrogels for biomedical applications. The bioresorbable properties of conjugated hydrogels by hydrolysis of the PLA segment and the rate of bioresorption of different elastin-PNPHO hydrogels in physiological environments were assessed.

Bioresorbability of Hydrogels

As discussed above, the degradation of hydrophobic domains (HEMA-PLA) in PNPHO and retention of hydrophilic segments (OEGMA) may result in increasing the LCST and dissolution of conjugated polymer in the body. The accelerated hydrolysis was conducted by immersing the sample in a sodium hydroxide solution (1 M) for a period of three weeks at 4° C. After this period, the suspension was neutralized with 10 M hydrochloride solution. The effect of PLA hydrolysis on the stability of the protein-PNPHO conjugate in physiological conditions was examined. Four different copolymers with the highest conjugation efficiencies $PNPHO_{11(3)5}$, $PNPHO_{11(3)8}$, $PNPHO_{8(6)5}$, and $PNPHO_{8(6)8}$ were selected for this study (as mentioned above). After hydrolysis, the characteristic peak of PLA at 5.1 ppm in $^1H$ NMR spectra of these copolymers disappeared, confirming the cleavage of PLA. The hydrolyzed copolymers were then conjugated with elastin.

Figure 8:
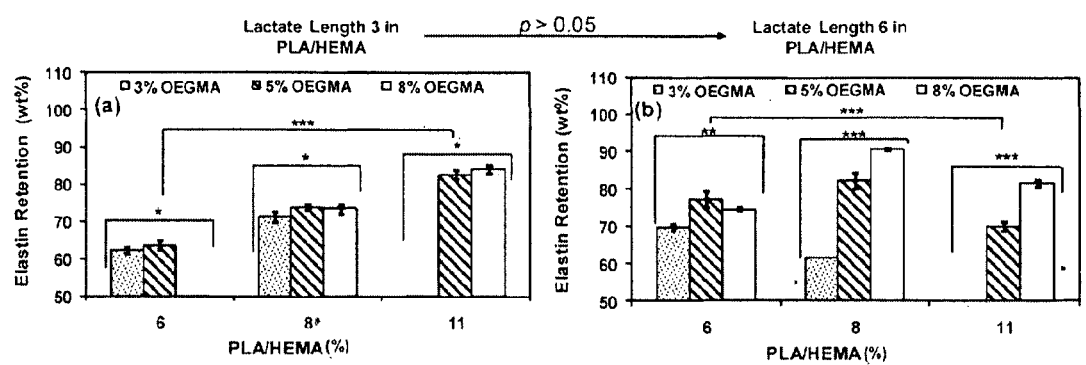
FIG. 8. Elastin conjugation efficiency to different copolymers. Elastin concentration was measured after 24 hr incubation in PBS at 37° C. HEMA-PLA with lactate number of 3 (a) and 6 (b).

The rheological properties of conjugated copolymer were compared at different temperatures before and after hydrolysis. Results presented in FIG. 8(a) underline the significant shift of gelling temperature to above 37° C. for hydrogels formed with hydrolyzed copolymers. For instance, the gelling temperature of $PNPHO_{11(3)8}$ after accelerated degradation was significantly (p<0.001) increased from 20.1±1.0° C. to 42.2±3.1° C. This result suggested that the copolymers turned became soluble at 37° C. following the cleavage of polylactide residues in the HEMA-PLA backbone of the copolymer. For many biomedical applications, such as in vivo tissue growth, the normal rate of degradation in physiological environment is an important factor.

Figure 9:
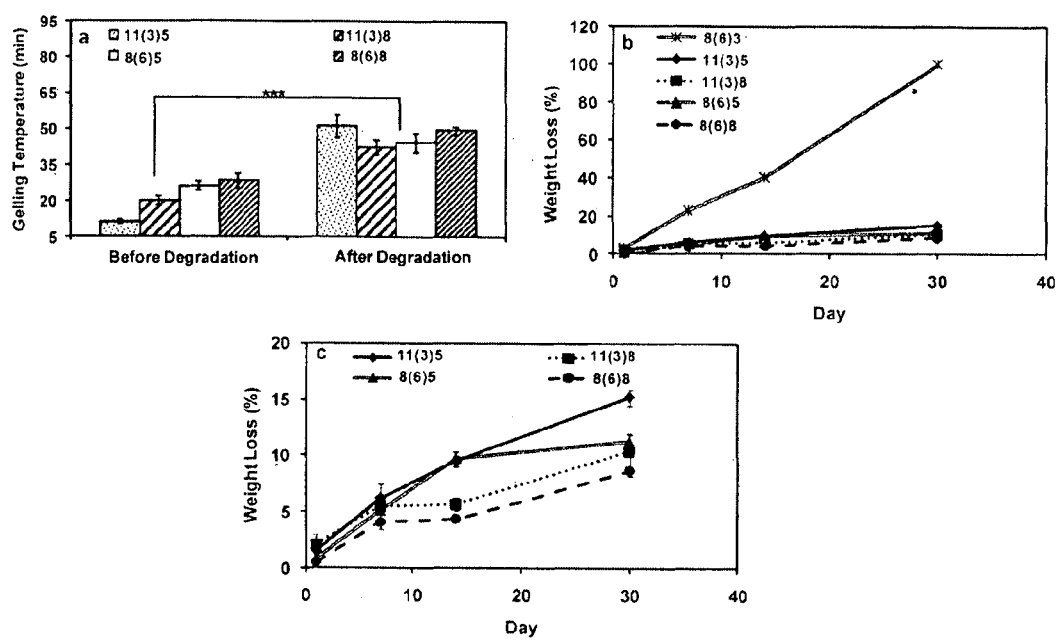
FIG. 9. Gelling temperature of biopolymer precursors formed with copolymer before and after degradation (a) and weight loss of different biopolymer hydrogels over time in PBS at 37° C. (b).

The Bioresorption Rate of Protein-PNHPO Hydrogels in the Physiological Environment Four compositions of copolymers with the highest bioconjugation efficiencies ($PNPHO_{11(3)5}$, $PNPHO_{11(3)8}$, $PNPHO_{8(6)5}$, and $PNPHO_{8(6)8}$) along with $PNPHO_{8(6)3}$ as a control were used to study the degradation and bioresorption conjugate hydrogels in confined environment at 37° C. in PBS. These hydrogels were soaked in PBS at 37° C. for 30 days and a gravimetric technique was used to determine the weight loss ratio of hydrogels in different time intervals. Results showed that the copolymers with high conjugation efficiency exhibited a significantly (p<0.001) lower degradation rate compared to $PNPHO_{8(6)3}$ with conjugation efficiency of 60%, as shown in FIG. 9(b). The formation of covalent bonds between elastin and copolymer impeded the formation of non-specific bonds of the copolymer molecule with itself and with elastin. The formation of non-specific bonds in complex molecule structures may lead to high degradation rate and weigh loss in hydrogels. PNPHO copolymers with high conjugation efficiency may form covalent bonds with elastin, which would inhibit formation of non-specific interactions of the copolymer chain with itself and elastin.

Results showed that all four biopolymers with high conjugation efficiency exhibited relatively low (<15%) weight loss within 30 days of incubation in PBS as shown in FIG. 9(c). During the first 7 days, there was no significant difference between the degradation rate of all copolymers with different hydrophilic and hydrophobic content (p>0.05). After 14 days of incubation, the copolymers with higher content of OEGMA ($pNPHO_{11(3)8}$ and $pNPHO_{8(6)8}$) and higher conjugation efficiency exhibited relatively lower weight loss (p<0.05) compared to the other two copolymers with OEGMA content of 5 mol %. This result was in agreement with our previous data that the copolymers with a higher bioconjugation ratio could retain their structure for a longer period of time.

The elastin-copolymer hydrogels formed with the optimum compositions of copolymer could retain 85% of their initial weight after 30 days of incubation in PBS. In contrast, Guan et al. reported approximately 90% of weight loss for hydrogels formed by conjugation of collagen and poly (NIPAAm-co-AAc-co-NAS-co-HEMA-PLA) after 21 days.[9] The higher stability of the hydrogels of the present invention was due to the high conjugation capacity of PNPHO copolymer. High stability of PNPHO in the physiological environment was comparable with other synthetic based injectable copolymers such as poly(NIPAAm-co-HEMA-co-methacrylate-polylactide (MAPLA)). This copolymer exhibited approximately 80% weight retention after 30 days of incubation in PBS at 37° C. However, this copolymer however had no functional group that can bond to proteins. The presence of facial active sites in PNPHO imparts protein conjugation capacity to this injectable system. This property of PNPHO copolymer may pass on superior biological properties to the injectable system and make it more favourable for different biomedical applications such as biofactor delivery and in vivo tissue growth.

the Effect of Conjugation Ratio on Structural Retention of Hydrogels

Any biomaterial used for tissue engineering applications must bind strongly to host tissue to promote tissue formation by accelerating cell migration within the structure. In addition, the biomaterial must exhibit good structural retention over time to promote integration of regenerated tissue with the surrounding environment. Commercially-available tissue glues, based on fibrins, are the current gold standard for surgical applications due to their non-cytotoxic properties. Their application, however, is limited due to the very high degradation rate. In particular, presence of chondrogenesis cells dramatically increases the degradation rate of these types of tissue glues. More recently, chondroitin sulphate-based glues were synthesized to covalently bond cartilage with hydrogels. This approach promoted the structural stability of hydrogels. However, it requires invasive implantation techniques involving cartilage digestion and UV cross-linking. To address this problem, chondroitin sulphate-PEG gels were designed to covalently bind with primary amines of collagen by formation of amide bonds in a physiological environment. These hydrogels, however, were not permissive for chondrocyte ingrowth and cartilage remodeling.

The ability of hydrogels to retain their structural integrity at the implanted sites is important in developing a suitable biomaterial for tissue repair. The structural integrity of protein-PNPHO hydrogels in a physiological environment was studied. Results showed that the chemical conjugation between protein and copolymer plays an important role in achieving structural integrity of hydrogels.

Figure 10:
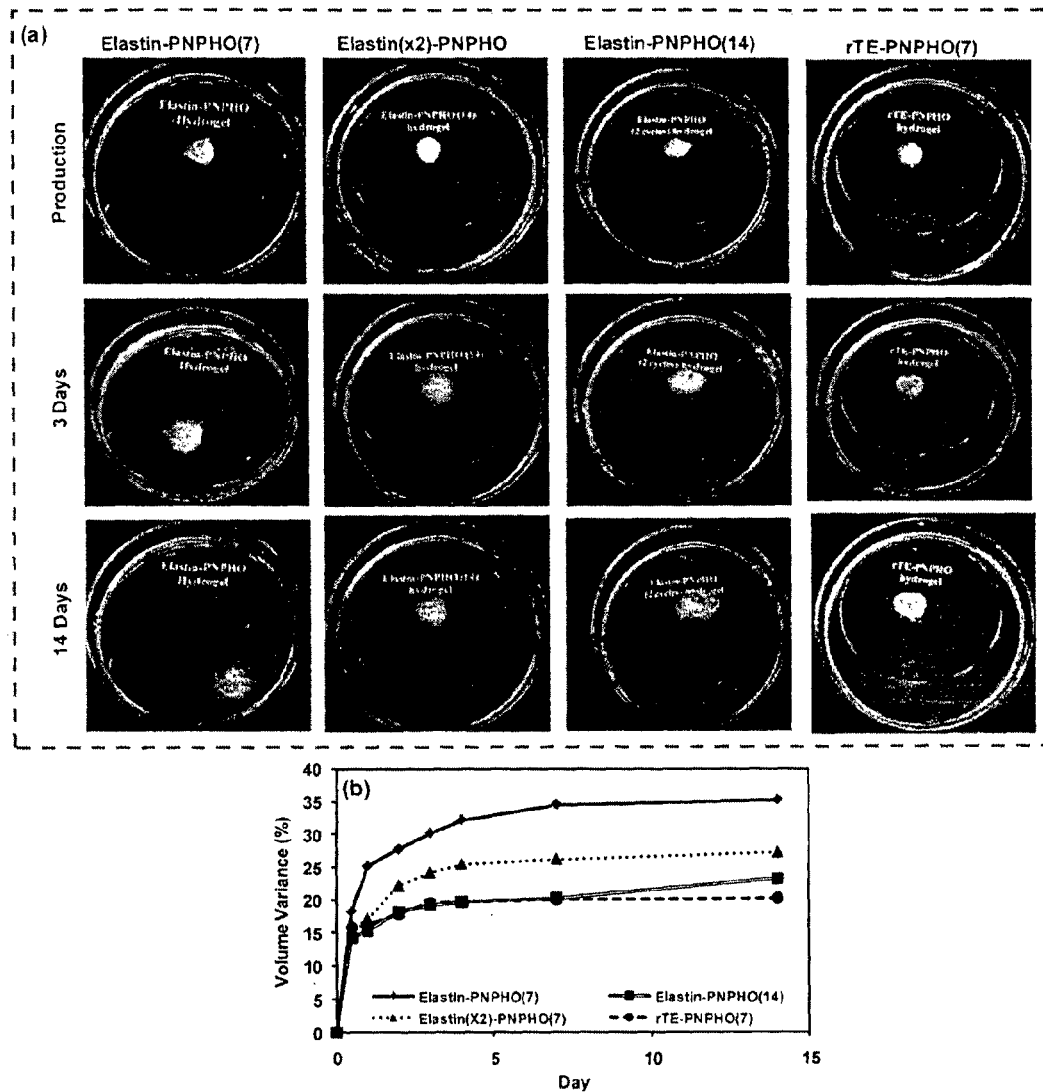
FIG. 10. Structural retention of protein-PNPHO hydrogels with different degrees of conjugation (a), and the effect of conjugation level on volume variances of hydrogels (b).

The degree of chemical conjugation between protein and copolymer was enhanced by having two-stage elastin-PNPHO conjugation, increasing facial active sites in copolymer, or using recombinant tropoelastin (rTE) to conjugate with PNPHO. In this part of study, $PNPHO_{8(6)5}$ was used. In a two-stage conjugation process, elastin-$PNPHO_{8(6)5}$ powder was dissolved in elastin solution instead of PBS to increase the conjugation ratio between elastin and copolymer (elastin(2×)-$PNPHO_{8(6)5}$). In the second approach, to elevate the conjugation degree, protein active site in the PNPHO copolymer was increased from 7 to 14 mol % by increasing NAS feed ratio in the synthesis of the copolymer, forming $PNPHO_{8(6)5-14}$. Alternatively, elastin was replaced with rTE with higher primary amine groups (35 lysine residues per molecule compared to α-elastin with less than 1%) to form a conjugate protein-$PNPHO_{8(6)5}$ system with a higher degree of conjugation. Hydrogels were soaked in PBS at 37° C. and their volume variations in different time intervals were recorded as shown in FIG. 10.

Results showed that the degree of chemical conjugation between protein and copolymer play an important role in structural retention of hydrogels. This was confirmed by lower volume variances of hydrogels with higher conjugation degrees compared to elastin-$PNPHO_{8(6)5}$. Chemical conjugation of elastin and copolymer was significantly increased in elastin(2×)-$PNPHO_{8(6)5}$ hydrogels by approximately two-fold. This effect yields to 50% less volume variance in elastin(2×)-$PNPHO_{8(6)5}$ after 14 days compared to elastin-$PNPHO_{8(6)5}$. The structural integrity of protein-copolymer hydrogel was further increased by elevating the protein reactivity of copolymer. Elastin-$PNPHO_{8(6)5-14}$ exhibited significantly higher structural integrity in physiological condition compared to elastin-$PNPHO_{8(6)5}$. By using rTE (which possesses a higher number of primary amine groups) the conjugation of protein and copolymer was also increased and the rTE-$PNPHO_{865}$ hydrogel possessed the highest structural integrity in a physiological environment after 14 days. This hydrogel exhibited less than 20% of volume variance within this period. These results show that the degree of chemical conjugation between protein and copolymer plays an important role in the stability and physical properties of a conjugated system.

Biological Studies

Human Skin Fibroblast Cells

Figure 11:
FIG. 11. Light microscopy image of fibroblast growing on tissue engineering flask after 24 hours (a) and 48 hours (b) at the vicinity of elastin-PNPHO$_{8(6)5}$ hydrogels.

Human skin fibroblast cells (GM3348) were cultured in the vicinity of a conjugated hydrogel to assess the cytocompatibility of elastin-PNPHO hydrogels. An elastin and PNPHO solution was formed by using sterilized PBS. Following gelation, hydrogels were washed with pre-warmed PBS for three times to remove all unreacted proteins and copolymer. The hydrogels (without any further sterilization) were then equilibrated in media (DMED, 10% FBS, and pen-strep) overnight at 37° C. The cells were then cultured at $2 \times 10^5$ cell/well in 6 well-plate at the vicinity of conjugated hydrogels. Cell proliferation on the well surface was studied with light microscopy analysis to assess the in vitro cytocompatibility of hydrogels. The results in FIG. 11 show that after 72 hours, fibroblasts were alive and proliferated close to the hydrogel. This result confirms that the conjugated hydrogels are cytocompatible and the degradation products are not cytotoxic.

Figure 12:
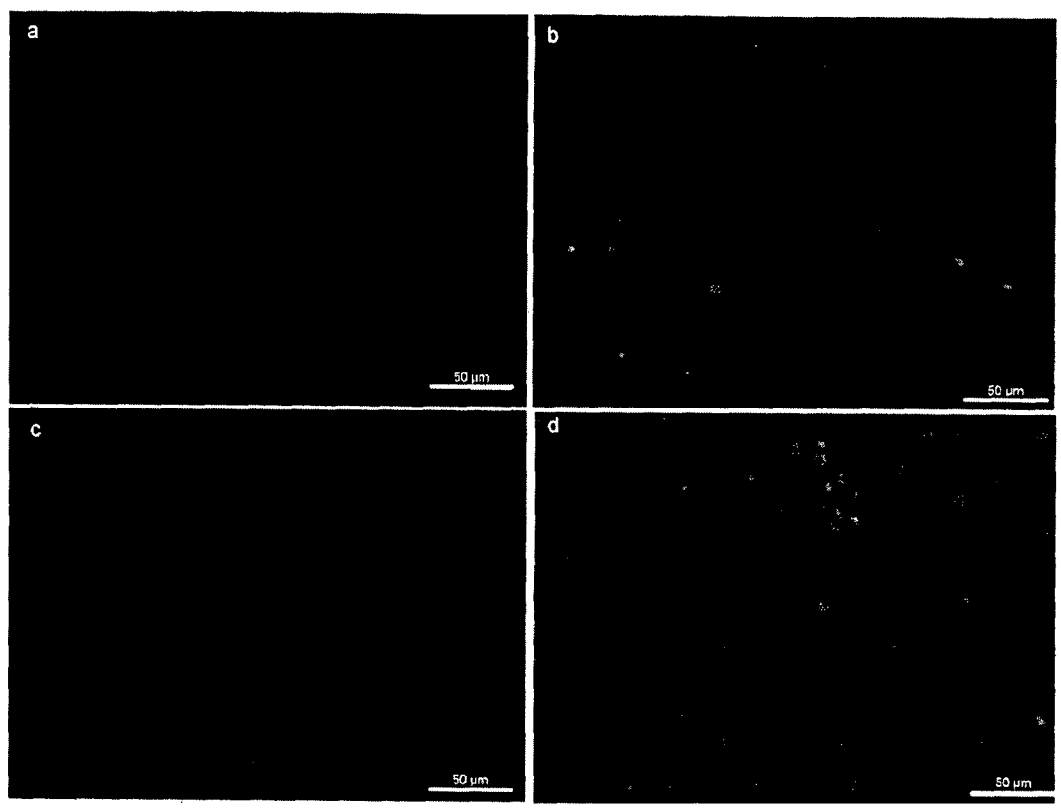
FIG. 12. Hoechst 33258 nucleolus staining of fibroblasts, encapsulated within elastin-PNPHO hydrogel after 24 hours (a) and 72 hours ((b)-(d)).

Cell encapsulation capability of conjugated hydrogels was also assessed, using fibroblasts. A highly concentrated cell suspension was mixed with an elastin-PNPHO solution at room temperature. This suspension was then incubated at 37° C., followed by gradual addition of media (DMEM, 10% FBS and pen-strep) to the hydrogels. Hoechst 33258 nucleolus staining was used to visualize fibroblast cells, encapsulated within the structure of hydrogels. The results in FIG. 12 show that the cell population was significantly increased from day 1 to day 3 within the elastin-PNPHO hydrogels. This result confirms the cytocompatability of this conjugated hydrogel.

Chondrocytes

Figure 13:
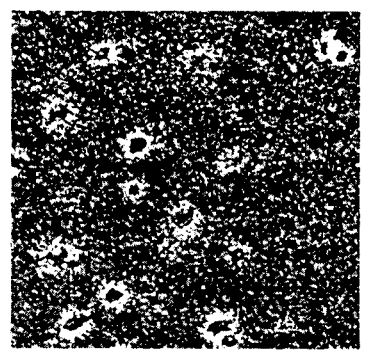
FIG. 13. Cryosection showing primary ovine chondrocytes (some dividing) in lacunae in an elastin hydrogel (a), and adjacent hematoxylin-stained section confirming viable chondrocytes (b). Scale bar is 100 µm.
Figure 13:
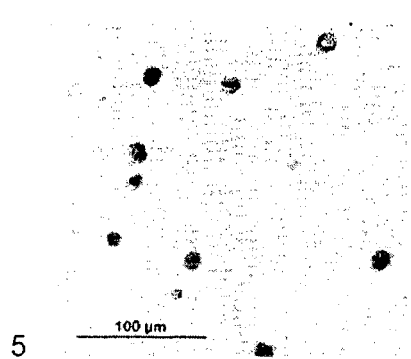

Our results demonstrate the feasibility of combining PNPHO, elastin and primary chondrocytes to the same viable cell densities as seen in sheep cartilage (FIG. 13). The embedded chondrocytes persist anaerobically in lacunae like they do in native cartilage. This result underlines the biocompatibility of the synthesized polymer and potential of using this construct for cartilage repair.

It will be understood that the invention disclosed and defined in this specification extends to all alternative combinations of two or more of the individual features mentioned or evident from the text or drawings. All of these different combinations constitute various alternative aspects of the invention.

REFERENCES

1. Vinatier, C. et al (2009) "Cartilage engineering: a crucial combination of cells, biomaterials and biofactors", *Trends in Biotechnology* 27(5):307-314.
2. van Donkelaar, C. C. and Schulz, R. M. (2008) "Review on patents for mechanical stimulation of articular cartilage tissue engineering", Recent Patents on *Biomedical Engineering* 1(1): 1-12.

3. Chung, C. and Burdick, J. A. (2008) "Engineering cartilage tissue", *Advanced Drug Delivery Reviews* 60: 243-262.
4. Lee, H. J., of al (2006) "Collagen mimetic peptide-conjugated photopolymerizable PEG hydrogel", *Biomaterials* 27: 5268-5276.
5. Gennaro, A. R., *Remington: The Science and Practice of Pharmacy*, 21st ed. (2006), Lippincott Williams & Wilkins.
6. Dijk-Wolthuis, W. van et al. (1997) "A new class of polymerizable dextrans with hydrolyzable groups: hydroxyethyl methacrylated dextran with and without oligolactate spacer", *Polymer* 38(25):6235-6242.
7. Mercado, A. E. et al: (2009) "Release characteristics and osteogenic activity of recombinant human bone morphogenetic protein-2 grafted to novel self-assembled poly (lactide-co-glycolide fumarate) nanoparticles", *Journal of Controlled Release* 140(2):148-156.
8. Bradford, M. M. (1976) "A rapid and sensitive method for the quantitation of microgram quantities of protein utilizing the principle of protein-dye binding", *Analytical Biochemistry* 72(1-2):248-254.
9. Guan, J. et al. (2008) "Protein-Reactive, Thermoresponsive Copolymers with High Flexibility and Biodegradability", *Biomacromolecules* 9: 1283-1292.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A polymer for forming a hydrogel, the polymer comprising:
   a backbone chain comprising portions of a first monomer, a second monomer, and third monomer, wherein:
   the first monomer comprises a polyether side chain that comprises a moiety selected from the group consisting of polyethylene glycol (PEG), oligo(ethylene glycol) (OEG), polyethylene oxide-co-propylene oxide (PPO), co-polyethylene oxide block or random copolymers, and polyvinyl alcohol (PVA);
   the second monomer comprises a methacrylate or a polyester side chain that comprises a moiety selected from the group consisting of hydroxyethyl methacrylate (HEMA), poly(lactic acid), poly(caprolactone), poly (glycolide), poly(glycolide-co-lactide), poly(glycolide-co-caprolactone), and random co-polymers thereof; and
   the third monomer comprises a protein-reactive side chain that comprises a moiety selected from the group consisting of N-hydroxysuccinimide (NHS), N-hydroxysulfosuccinimide (SNHS), N-hydroxyethoxylated succinimide (ENHS), and N-acryloxysuccinimide (NAS);
   wherein each of the polyether side chain, the methacrylate or the polyester side chain, and the protein-reactive side chain extends from the backbone chain to form a free end.

2. The polymer of claim 1, wherein the backbone chain further comprises a portion of a fourth monomer, wherein the fourth monomer comprises N-isopropylacrylamide.

3. The polymer of claim 1, wherein the moiety of the polyether side chain of the first monomer is OEG.

4. The polymer of claim 1, wherein the second monomer comprises the random co-polymer HEMA-poly(lactic acid).

5. The polymer of claim 1, wherein the moiety of the protein reactive site of the third monomer is NAS.

6. The polymer of claim 1, wherein the polymer is a polymer of formula (IIa):

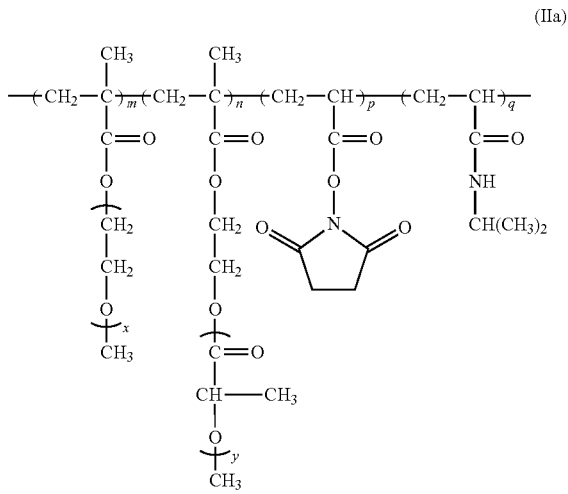

wherein m is an integer from 1 to 10, n is an integer from 1 to 10, p is an integer from 1 to 10, q is an integer from 1 to 10, x is an integer from 1 to 1000, and y is an integer from 1 to 1000.

7. A composition for forming a hydrogel, the composition including an extra-cellular matrix protein and the polymer of claim 1.

8. The composition of claim 7, wherein the extra-cellular matrix protein is collagen.

9. A hydrogel including water, an extra-cellular matrix protein, and the polymer of claim 1.

10. The hydrogel of claim 9, wherein the hydrogel is formed by adding water to the extracellular matrix protein and the polymer.

11. The hydrogel of claim 9, wherein the hydrogel further includes one or more cells to assist in the repair of biological tissue.

12. The hydrogel of claim 9, wherein the extra-cellular matrix protein is collagen.

13. The polymer of claim 1, wherein the polymer is a polymer of formula (Ia):

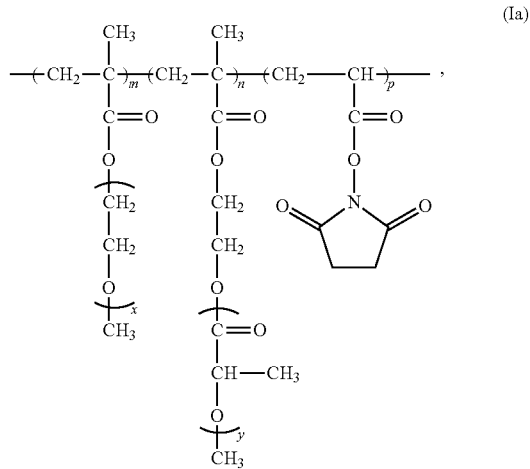

wherein m is an integer from 1 to 10, n is an integer from 1 to 10, p is an integer from 1 to 10, x is an integer from 1 to 1000, and y is an integer from 1 to 1000.

* * * * *